(12) United States Patent
Varone et al.

(10) Patent No.: US 12,187,996 B2
(45) Date of Patent: Jan. 7, 2025

(54) OPEN-TOP MICROFLUIDIC DEVICES AND METHODS FOR SIMULATING A FUNCTION OF A TISSUE

(71) Applicant: President and Fellows of Harvard College, Cambridge, MA (US)

(72) Inventors: Antonio Varone, Cambridge, MA (US); Norman Wen, Cambridge, MA (US); Daniel Levner, Cambridge, MA (US); Richard Novak, Cambridge, MA (US); Lori McPartlin, Cambridge, MA (US); Donald E. Ingber, Cambridge, MA (US); Youngjae Choe, Cambridge, MA (US); Lian Leng, Cambridge, MA (US); Justin K. Nguyen, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 18/056,035

(22) Filed: Nov. 16, 2022

(65) Prior Publication Data
US 2023/0159872 A1    May 25, 2023

Related U.S. Application Data

(63) Continuation of application No. 15/781,078, filed as application No. PCT/US2016/064798 on Dec. 2, 2016, now Pat. No. 11,505,773.
(Continued)

(51) Int. Cl.
*C12M 3/06* (2006.01)
*B01L 3/00* (2006.01)
(Continued)

(52) U.S. Cl.
CPC ............ *C12M 23/16* (2013.01); *C12M 21/08* (2013.01); *C12M 25/02* (2013.01); *C12M 25/14* (2013.01);
(Continued)

(58) Field of Classification Search
None
See application file for complete search history.

(56) References Cited

U.S. PATENT DOCUMENTS

| 7,485,454 B1 | 2/2009 | Jury |
| 7,807,453 B2 | 10/2010 | Quinn |

(Continued)

FOREIGN PATENT DOCUMENTS

| EP | 2639293 | 10/2021 |
| JP | 2011-092180 | 5/2011 |

(Continued)

OTHER PUBLICATIONS

Iliescu et al., A practical guide for the fabrication of microfluidic devices using glass and silicon, 2012, Biomicrofluidics, 6, 016505 (Year: 2012).*

(Continued)

*Primary Examiner* — Holly Kipouros
(74) *Attorney, Agent, or Firm* — Nixon Peabody LLP

(57) ABSTRACT

A device for simulating a function of a tissue includes a first structure, a second structure, and a membrane. The first structure defines a first chamber. The first chamber includes a matrix disposed therein and an opened region. The second structure defines a second chamber. The membrane is located at an interface region between the first chamber and the second chamber. The membrane includes a first side facing toward the first chamber and a second side facing toward the second chamber. The membrane separates the first chamber from the second chamber.

7 Claims, 18 Drawing Sheets

Related U.S. Application Data

(60) Provisional application No. 62/263,225, filed on Dec. 4, 2015.

(51) Int. Cl.
| | |
|---|---|
| *C12M 1/00* | (2006.01) |
| *C12M 1/12* | (2006.01) |
| *C12M 1/34* | (2006.01) |
| *C12M 3/00* | (2006.01) |
| *C12M 3/04* | (2006.01) |
| *C12N 5/071* | (2010.01) |
| *C12N 5/077* | (2010.01) |

(52) U.S. Cl.
CPC ......... *C12N 5/0629* (2013.01); *C12N 5/0656* (2013.01); *C12N 5/0679* (2013.01); *C12N 5/069* (2013.01); *B01L 3/5027* (2013.01); *B01L 2300/069* (2013.01); *C12M 3/04* (2013.01); *C12M 29/10* (2013.01); *C12M 41/46* (2013.01)

(56) References Cited

U.S. PATENT DOCUMENTS

| | | | |
|---|---|---|---|
| 8,647,861 B2 | 2/2014 | Ingber | |
| 10,988,723 B1 | 4/2021 | Hatch et al. | |
| 2003/0017142 A1 | 1/2003 | Toner et al. | |
| 2006/0240548 A1 | 10/2006 | Deutsch | |
| 2007/0141552 A1 | 6/2007 | Warren | |
| 2007/0292939 A1* | 12/2007 | Chen | C12M 25/14 435/288.3 |
| 2011/0053207 A1 | 3/2011 | Hoganson et al. | |
| 2011/0053270 A1 | 3/2011 | Chang et al. | |
| 2011/0081677 A1 | 4/2011 | Luo | |
| 2011/0082056 A1 | 4/2011 | Park | |
| 2011/0183312 A1 | 7/2011 | Huang | |
| 2011/0275543 A1 | 11/2011 | Deutsch | |
| 2012/0135452 A1* | 5/2012 | Shuler | C12M 29/00 435/395 |
| 2012/0164679 A1 | 6/2012 | Vrouwe | |
| 2012/0195810 A1 | 8/2012 | Cohen | |
| 2014/0038279 A1 | 2/2014 | Ingber | |
| 2014/0055853 A1 | 2/2014 | Corwin | |
| 2014/0093905 A1 | 4/2014 | Inger | |
| 2014/0186414 A1* | 7/2014 | Ingber | A61P 7/04 435/2 |
| 2014/0335496 A1* | 11/2014 | Grego | C12M 21/08 434/272 |
| 2014/0342445 A1 | 11/2014 | Ingber et al. | |
| 2014/0349396 A1 | 11/2014 | West | |
| 2015/0004077 A1 | 1/2015 | Wikswo | |
| 2015/0252328 A1 | 9/2015 | Woodruff et al. | |
| 2016/0136333 A1* | 5/2016 | Reichmann | C12M 23/48 425/406 |

FOREIGN PATENT DOCUMENTS

| | | |
|---|---|---|
| JP | 2011-528232 | 5/2011 |
| KR | 2014-0040704 | 4/2014 |
| WO | 2004/059299 A1 | 7/2004 |
| WO | 2010/122945 A1 | 10/2010 |
| WO | 2013-085909 | 6/2013 |
| WO | 2015-138032 | 9/2015 |
| WO | 2015138034 A2 | 9/2015 |

OTHER PUBLICATIONS

Notice of Eligibility of Grant and Examination Report in Singapore Application No. 11201804706U, dated Aug. 4, 2022 (6 pages).

Bhatia et al., "Microfluidic organs-on-chips,"Nature biotechnology, Aug. 5, 2014 (Aug. 5, 2014), vol. 32, No. 8, pp. 760-772.

Carlson, M.W. et al., "Three-Dimensional Tissue Models of Normal and Diseased Skin," Current Protocols in Cell Biology, Supplement 41, Dec. 2008, pp. 19.9.1-19.9.17 (17 pages).

De Oliveira, Z.N.P et al., "Immunological mapping in hereditary epidermolysis bullosa," An Bras Dermatol., 85(6), 2010, Rio de Janeiro, pp. 856-861 (6 pages).

Jean, J. et al., "Bioengineered Skin: The Self-Assembly Approach," Journal of Tissue Science & Engineering, 2011, S:5, DOI: 10.4172/2157-7552.S5-001 (10 pages).

Keenan, T.M. et al., "A New Method for Studying Gradient-Induced Neutrophil Desensitization Based on an Open Microfluidic Chamber," Lab Chip, Jan. 7, 2010, 10(1), pp. 116-122, DOI:10.1039/b913494h (14 pages).

Wagner et al., "A Dynamic Multi-Organ-Chip for Long-Term Cultivation and Substance Testing Proven by 3D Human Liver and Skin Tissue Co-Culture," Lab on a Chip, May 7, 2013 (May 7, 2013), vol. 13, pp. 3538-3547.

Partial European Search Report in European Patent Application No. 16871655.3, dated May 19, 2019 (11 pages).

Lovchik, R.D. et al., "Overflow Microfluidic Networks," 14th International Conference on Miniaturized Systems for Chemistry and Life Sciences, Oct. 3-7, 2010, Groningen, The Netherlands, pp. 989-991 (3 pages).

Maas-Szabowski, N. et al., "Keratinocyte Growth Regulation in Defined Organotypic Cultures Through IL-1-Induced Keratinocyte Growth Factor Expression in Resting Fibroblasts," Journal of Investigative Dermatology, 2000, 114, pp. 1075-1084 (10 pages).

Wright, G.A. et al., "On-Chip Open Microfluidic Devices for Chemotaxis Studies," Microsc Microanal., Aug. 2012, 18(4), pp. 816-828, DOI:10.1017/S1431927612000475 (22 pages).

"A new—and heart-warming—biomaterial for tissue engineering?", Harsjorg Wyss Institute for Biologically Inspired Engineering, May 7, 2013 (3 pages).

International Search Report in International Application No. PCT/US2016/064798, mailed Mar. 17, 2017 (4 pages).

Written Opinion in International Application No. PCT/US2016/064798, mailed Mar. 17, 2017 (7 pages).

Tenenbaum-Katan et al., "Biomimetics of fetal alveolar flow phenomena using microfluidics," Biomicrofluidics 9, pp. 014120-0-014120-13 (2015) 14 pages.

Muller et al., "Culturing of Human Nasal Epithelial Cells at the Air Liquid Interface", 2013, J. Vis. Exp. (80), e50646, pp. 1-7 (Year: 2013).

\* cited by examiner

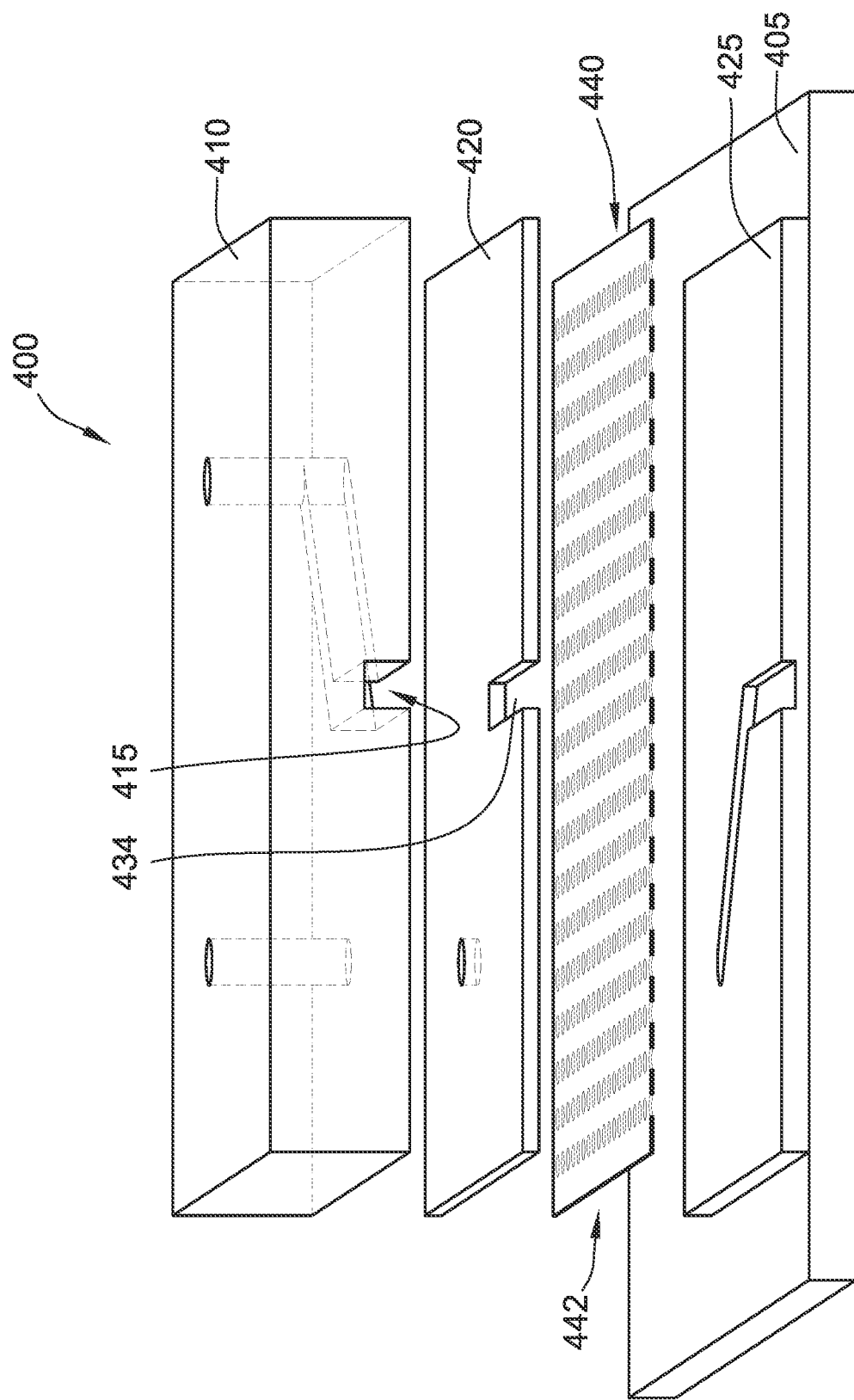

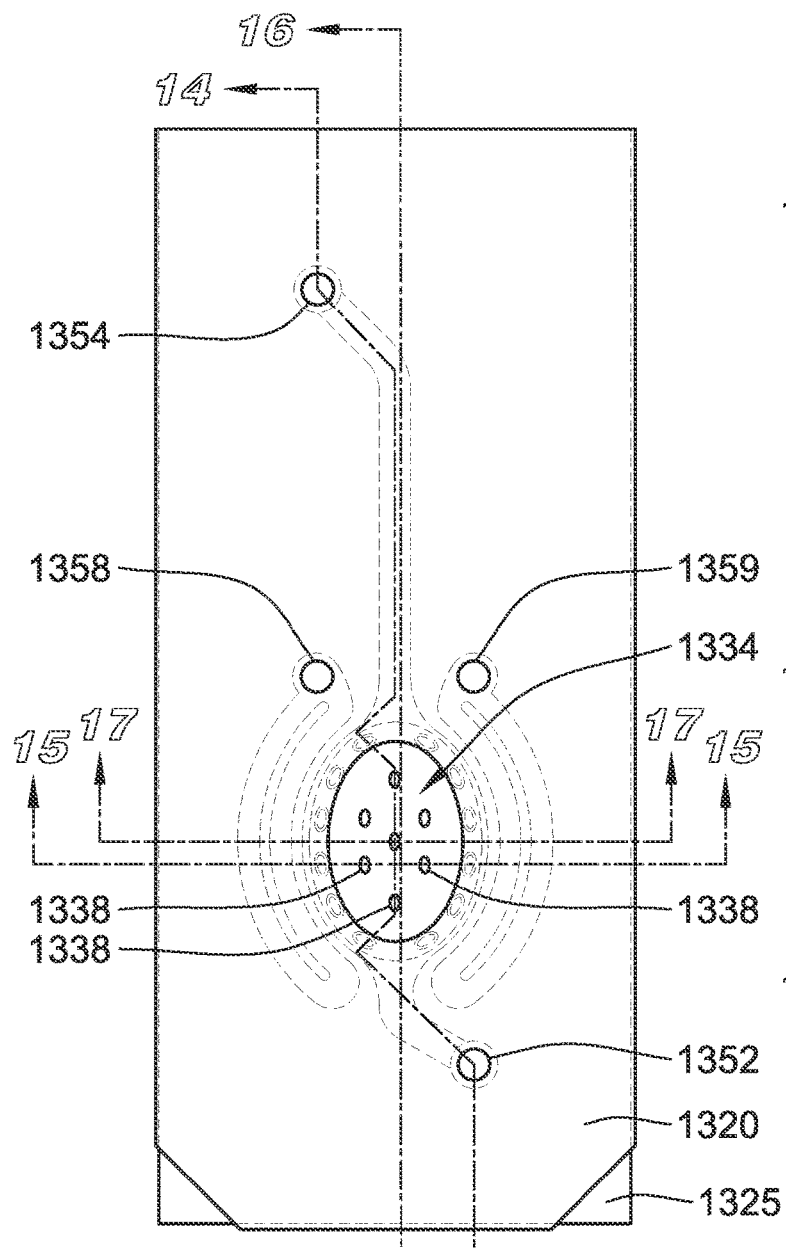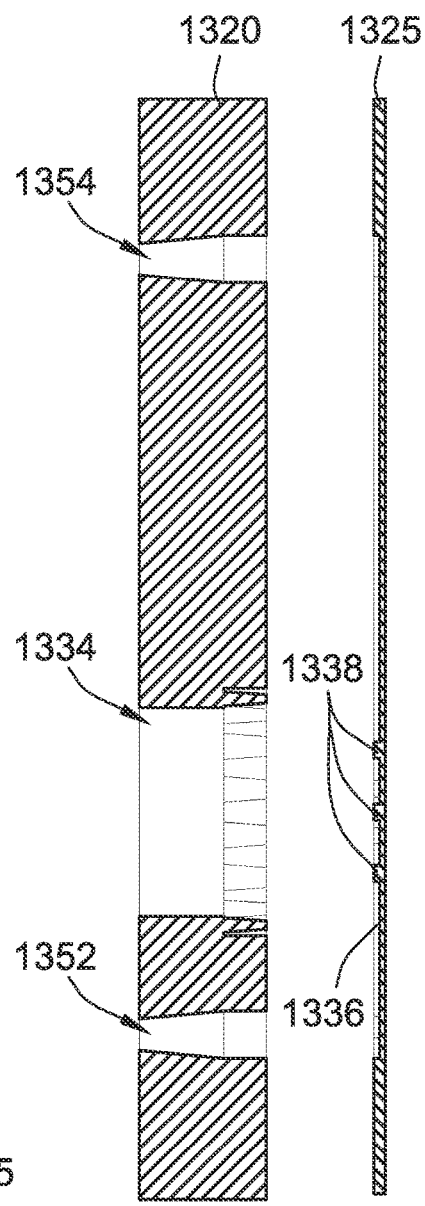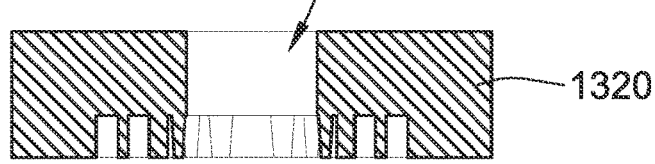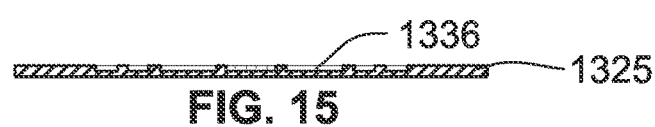
FIG. 13
FIG. 14
FIG. 15

OPEN-TOP MICROFLUIDIC DEVICES AND METHODS FOR SIMULATING A FUNCTION OF A TISSUE

CROSS-REFERENCE TO RELATED APPLICATIONS

This application is a continuation of U.S. Non-Provisional application Ser. No. 15/781,078, filed Jun. 1, 2018, now U.S. Pat. No. 11,505,773, issued Nov. 2, 2022, which is a U.S. National Stage of International Application No. PCT/US2016/064798, filed Dec. 2, 2016, which claims priority to and the benefit under 35 U.S.C. § 119(e) to U.S. Provisional Application No. 62/263,225, filed Dec. 4, 2015, the contents of each of which are hereby incorporated by reference herein in their entireties.

GOVERNMENT SUPPORT

This invention was made with government support under grant no. W911NF-12-2-0036 awarded by U.S. Department of Defense, Advanced Research Projects Agency. The government has certain rights in the invention.

TECHNICAL FIELD

The present invention relates to cell culture systems and fluidic systems. More specifically, the invention relates to microfluidic devices and methods for simulating a function of a tissue.

BACKGROUND

In microfluidic devices that are designed for experimentation on cells, there is typically an "active area" at which the desired conditions or environments for cell culturing and experimentation are present. Other areas in the device serve other functions. It is often desirable to constrain the cells to the active area and avoid cells in the other areas. In one exemplary microfluidic device having a membrane that separates two microchannels, it is desirable to have the cells retained in the membrane region of the device, where cells can communicate through the membrane. On the other hand, it is desirable to avoid cells in the various fluid inlet and outlet channels that lead to and from the membrane region.

It is often desirable to limit the presence of cells or other biological elements within microdevices to the active region, for example, where the cell layers are separated by a porous membrane. Additionally, it is often desirable to constrain fluids to specific device areas, even if the device comprises elements that are not bonded. For example, fluidic seals are used when coupling non-bonded materials, such as membrane, to contain fluids and/or cells in the channels and chambers to minimize fluid, reagent or cell escape and growth between membranes and the sealing materials. Such cell escape or growth can cause unclear tissue boundaries, variability in bioassays and growth rates of tissue, or cell escape into the surrounding fluidic channels.

Fluids are typically moved through microfluidic devices for experimentation on cells using inlet and outlet ports accessible at a surface of the microfluidic device. Current microfluidic devices can be problematic for experimentation on topical treatments, the seeding of additional cells type, or for aerosol delivery for certain tissue types.

SUMMARY

According to one aspect of the present invention, a device for simulating a function of a tissue includes a first structure defining a first chamber. The first chamber includes a matrix disposed therein and includes an opened region. A second structure defines a second chamber. A membrane is located at an interface region between the first chamber and the second chamber. The membrane includes a first side facing toward the first chamber and a second side facing toward the second chamber. The membrane separates the first chamber from the second chamber.

According to another aspect of the present invention, a microfluidic device includes a gel chamber with a gel matrix disposed therein. The gel chamber includes an open top surface region. A fluidic chamber includes a first interface region that is formed between the gel chamber and the fluidic chamber. A membrane is disposed at the first interface region. The membrane includes a first side facing the gel chamber and a second side facing the fluidic chamber.

In a yet another aspect of the present invention, a method for creating a patterned gel in a device for simulating a tissue microstructure includes (a) providing a gel solution in a device, the device including a first chamber, a second chamber, and a membrane separating the first chamber from the second chamber, the first chamber comprising an opened region; (b) placing a plunger stamp into the first chamber through the opened region such that a textured bottom surface of the plunger stamp is in contact with the gel solution within the first chamber, wherein the textured bottom surface includes a pattern of features to be imprinted into the surface of the gel solution; (c) allowing the gel solution to solidify in the first chamber; and (d) removing the plunger stamp from the first chamber, thereby creating a patterned gel to simulate a tissue microstructure in the device.

In a yet another aspect of the present invention, a method of growing fibroblasts and keratinocytes includes (a) providing i) living fibroblasts, ii) living keratinocytes, and iii) a microfluidic device comprising first chamber with a extracellular matrix coating disposed therein, the first chamber in fluidic communication with a second chamber including a fluid source, the first and second chamber separated by a membrane; (b) seeding the extracellular matrix with the fibroblasts; (c) at least four days after the seeding of step (b), seeding the extracellular matrix with the keratinocytes at a ratio of at least 4 keratinocytes to 1 fibroblast; (d) at least four days after the seeding of step (c), initiating a recirculating air-liquid interface under conditions such that, after a number of days, keratinocytes are in multiple layers with numerous large cells indicating differentiation.

In a yet another aspect of the present invention, a method of growing fibroblasts and keratinocytes includes (a) providing i) living fibroblasts, ii) living keratinocytes, and iii) a microfluidic device comprising first chamber with a extracellular matrix coating disposed therein, the first chamber in fluidic communication with a second chamber including a fluid source, the first and second chamber separated by a membrane; (b) at day zero, seeding the extracellular matrix with the fibroblasts; (c) at between day six and day ten, seeding the extracellular matrix with the keratinocytes at a ratio of approximately 15 keratinocytes to 1 fibroblast; and (d) at between day thirteen and day sixteen, initiating a recirculating air-liquid interface under conditions such that, at day twenty-one or thereafter, keratinocytes are in multiple layers with numerous large cells indicating differentiation.

In a yet another aspect of the present invention, a method of seeding intestinal cells includes (a) providing a microfluidic device comprising a first chamber that includes a gel matrix disposed therein, a second chamber that is separated from the first chamber by a membrane, and the gel matrix positioned under a removable cover; (b) removing the removable cover thereby exposing the gel matrix; and (c) seeding the gel with intestinal cells.

In a yet another aspect of the present invention, a method of seeding lung epithelial cells includes (a) providing a microfluidic device comprising a first chamber and a second chamber, the second chamber separated from the first chamber by a membrane, the first chamber positioned under a removable cover; (b) removing the removable cover thereby creating an opened region over a first side of the membrane; and (c) seeding the first side of the membrane with lung epithelial cells.

In a yet another aspect of the present invention, a method of treating lung epithelial cells includes (a) providing a microfluidic device comprising a first chamber and a second chamber, the second chamber separated from the first chamber by a membrane, the membrane including lung epithelial cells on a side facing the first chamber, the cells positioned under a removable cover; (b) removing the removable cover thereby creating an opened region over the cells; and (iii) treating the lung epithelial cells with an agent.

Additional aspects of the invention will be apparent to those of ordinary skill in the art in view of the detailed description of various embodiments, which is made with reference to the drawings, a brief description of which is provided below.

BRIEF DESCRIPTION OF THE DRAWINGS

FIG. 4 illustrates an exploded perspective view of an exemplary cross-section through an open-top microfluidic device with a removable cover according to aspects of the present disclosure.

FIG. 13 illustrates a top view of an exemplary open-top microfluidic device including gel-anchoring pillars and membrane support posts according to aspects of the present disclosure.

FIGS. 14 and 15 illustrate cross-sectional views of the exemplary open-top microfluidic device of FIG. 13 according to aspects of the present disclosure.

Figure 1:
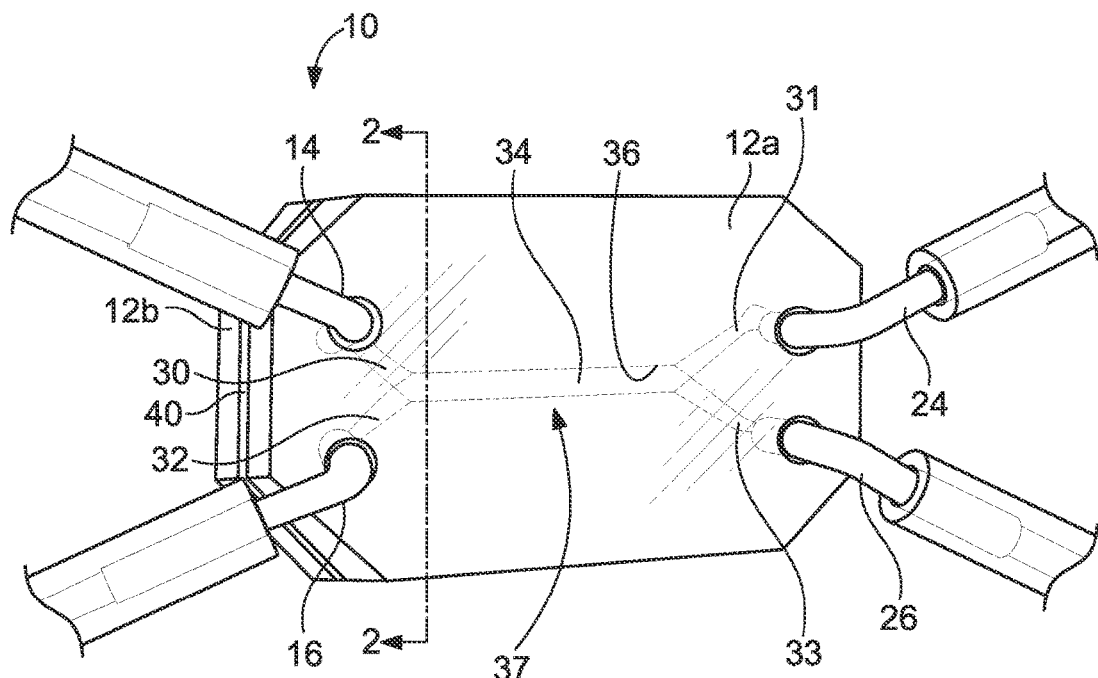
FIG. 1 illustrates an exemplary microfluidic device with a membrane region having cells thereon according to aspects of the present disclosure.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION

While this invention is susceptible of embodiment in many different forms, there is shown in the drawings and will herein be described in detail preferred aspects of the invention with the understanding that the present disclosure is to be considered as an exemplification of the principles of the invention and is not intended to limit the broad aspect of the invention to the embodiment illustrated. For purposes of the present detailed description, the singular includes the plural and vice versa (unless specifically disclaimed); the word "or" shall be both conjunctive and disjunctive; the word "all" means "any and all"; the word "any" means "any and all"; and the word "including" means "including without limitation."

Those of ordinary skill in the art will realize that the following description is illustrative only and is not intended to be in any way limiting. Other embodiments will readily suggest themselves to such skilled persons having the benefit of this disclosure. Reference will now be made in detail to implementations of the example embodiments as illustrated in the accompanying drawings. The same or similar reference indicators will be used throughout the drawings and the following description to refer to the same or like items. It is understood that the phrase "an embodiment" encompasses more than one embodiment and is thus not limited to only one embodiment.

As used herein, the term "rigid" refers to a material that is stiff and does not stretch easily, or maintains very close to its original form after a force or pressure has been applied to it. The term "elastomeric" as used herein refers to a material or a composite material that is not rigid as defined herein. An elastomeric material can be generally moldable, extrudable, cuttable, machinable, castable, and/or curable, and can have an elastic property that enables the material to deform (e.g., stretching, expanding, contracting, retracting, compressing, twisting, and/or bending) when subjected to a mechanical force or pressure and partially or completely resume its original form or position in the absence of the mechanical force or pressure. In some embodiments, the term "elastomeric" can also refer to a material that is flexible and/or stretchable but it does not resume its original form or position after pressure has been applied to it and removed thereafter. The terms "elastomeric" and "flexible" are used interchangeably herein.

The functionality of cells, tissue types, organs, or organ-components can be implemented in one or more microfluidic devices or "chips" that enable researchers to study these cells, tissue types, organs, or organ-components outside of the body while mimicking much of the stimuli and environment that the tissue is exposed to in-vivo. In some aspects, it is desirable to implement these microfluidic devices into interconnected components that can simulate groups of organs, organ-components, or tissue systems. In some cases it is desirable to configure the microfluidic devices so that they can be easily inserted and removed from an underlying fluidic system that connects to these devices in order to vary the simulated in-vivo conditions and organ systems.

Many of the problems associated with earlier systems can be solved by providing an open-top style microfluidic device that allows topical access to one or more parts of the device or cells that it comprises. For example, the microfluidic device can include a removable cover, that when removed, provides access to the cells of interest in the microfluidic device. In some aspects, the microfluidic devices include systems that constrain fluids, cells, or biological components to desired area(s). The improved systems provide for more versatile experimentation when using microfluidic devices, including improved application of treatments being tested, improved seeding of additional cells, and/or improved aerosol delivery for select tissue types. In a preferred embodiment, the open-top microfluidic device comprises a gel matrix.

The present disclosure additionally relates to organ-on-chips ("OOCs"), such as fluidic devices comprising one or more cells types for the simulation one or more of the function of organs or organ-components. Accordingly, the present disclosure additionally describes open-top organ-on-chips that solve problems associated with earlier fluidic systems. Without limitation, specific examples include models of skin, bronchial, and gut.

It is also desirable in some aspects to provide access to regions of a cell-culture device. For example, it can be desirable to provide topical access to cells to (i) apply topical treatments with liquid, gaseous, solid, semi-solid, or aerosolized reagents, (ii) obtain samples and biopsies, or (iii) add additional cells or biological/chemical components.

The present disclosure relates to fluidic systems that include a fluidic device, such as a microfluidic device with an opening that provides direct access to device regions or components (e.g. access to the gel region, access to one or more cellular components, etc.). Although the present disclosure provides an embodiment wherein the opening is at the top of the device (referred to herein with the term "open top"), the present invention contemplates other embodiments where the opening is in another position on the device. For example, in one embodiment, the opening is on the bottom of the device. In another embodiment, the opening is on one or more of the sides of the device. In another embodiment, there is a combination of openings (e.g. top and sides, top and bottom, bottom and side, etc.). While detailed discussion of the "open top" embodiment is provided herein, those of ordinary skill in the art will appreciate that many aspects of the "open top" embodiment apply similarly to open bottom embodiments, as well as open side embodiments or embodiments with openings in any other regions or directions, or combinations thereof. Similarly, the device need not remain "open" throughout its use; rather, as several embodiments described herein illustrate, the device may further comprise a cover or seal, which may be affixed reversibly or irreversibly. For example, removal of a removable cover creates an opening, while placement of the cover back on the device closes the device. The opening, and in particular the opening at the top, provides a number of advantages, for example, allowing (i) the creation of one or more gel layers for simulating the application of topical treatments on the cells, tissues, or organs, or (ii) the addition of chemical or biological components such as the seeding of additional cell types for simulated tissue and organ systems. The present disclosure further relates to improvement in fluidic system(s) that improve the delivery of aerosols to simulated tissue and organ systems, such as simulated lung tissues.

Furthermore, the present disclosure contemplates improvements to fluidic systems that include a fluidic device, such as a microfluidic device with an open-top region that reduces the impact of stress that can cause the delamination of tissue or related component(s) (e.g., such as a gel layer).

Improvements to microfluidic devices for simulating the function of a tissue are contemplated by the present disclosure that include one or more of an open-top microfluidic device with two or more chambers (e.g., microchannels) separated by a membrane. In some embodiments, one or more of the devices further comprises a gel in a chamber (e.g., microchannel or cavity) accessible through an opening, including but not limited to an open-top structure, of the microfluidic device. In some embodiments, the device further comprises a removable or permanent cover for the microfluidic device where the cover optionally has a fluidic chamber or microchannel therein. Other desirable improvements that are contemplated include a patterned gel in a microfluidic device. The present disclosure further describes a method for culturing cells in open-top devices. In some embodiments, the method comprises placing a gel into an open-top structure. In some embodiments, the method further comprises patterning the gel using a shaping device, such as a patterned plunger stamp, a shaping stamp, or similar devices. In some embodiments, the method comprises permanently or reversibly applying a cover or other shaping device to the open-top.

The present disclosure further relates to the use of fluidic systems that include a fluidic device, such as a microfluidic device with an open-top, to construct a model simulating the structure and/or one or more functions of, for example, skin, bronchial, or gut. In some embodiments, these models benefit from the presence of gels, which for example, can provide a mechanical, biochemical environment for one or more cells types, augment the mass-transport characteristics, or provide an additional compartment that may be used, for example, to house an additional cell type (e.g. fibroblasts).

A system that provides for the use of a gel can be particularly desirable for a skin model. For example, the current state-of-the-art skin model, the living skin equivalent (LSE), is a 3D gel, 2 mm to 3 mm thick, that is embedded with fibroblasts with differentiated keratinocytes on top of the gel. The actual thickness of the gel can range from 0.1 mm to 5 mm. It is known that a 3D gel is preferred to properly culture the fibroblasts that, in turn, enables keratinocytes to fully differentiate. An open-top architecture as described by the present disclosure is desirable because it enables LSE-like and similar cultures of fibroblasts and keratinocytes, while further allowing the introduction of an endothelial layer, the application of shear forces, and the application of stretching to create a more physiologically relevant model. Each of these optional features, individually and collectively, provides desirable improvements over current state-of-the-art LSE-like skin models.

Figure 2:
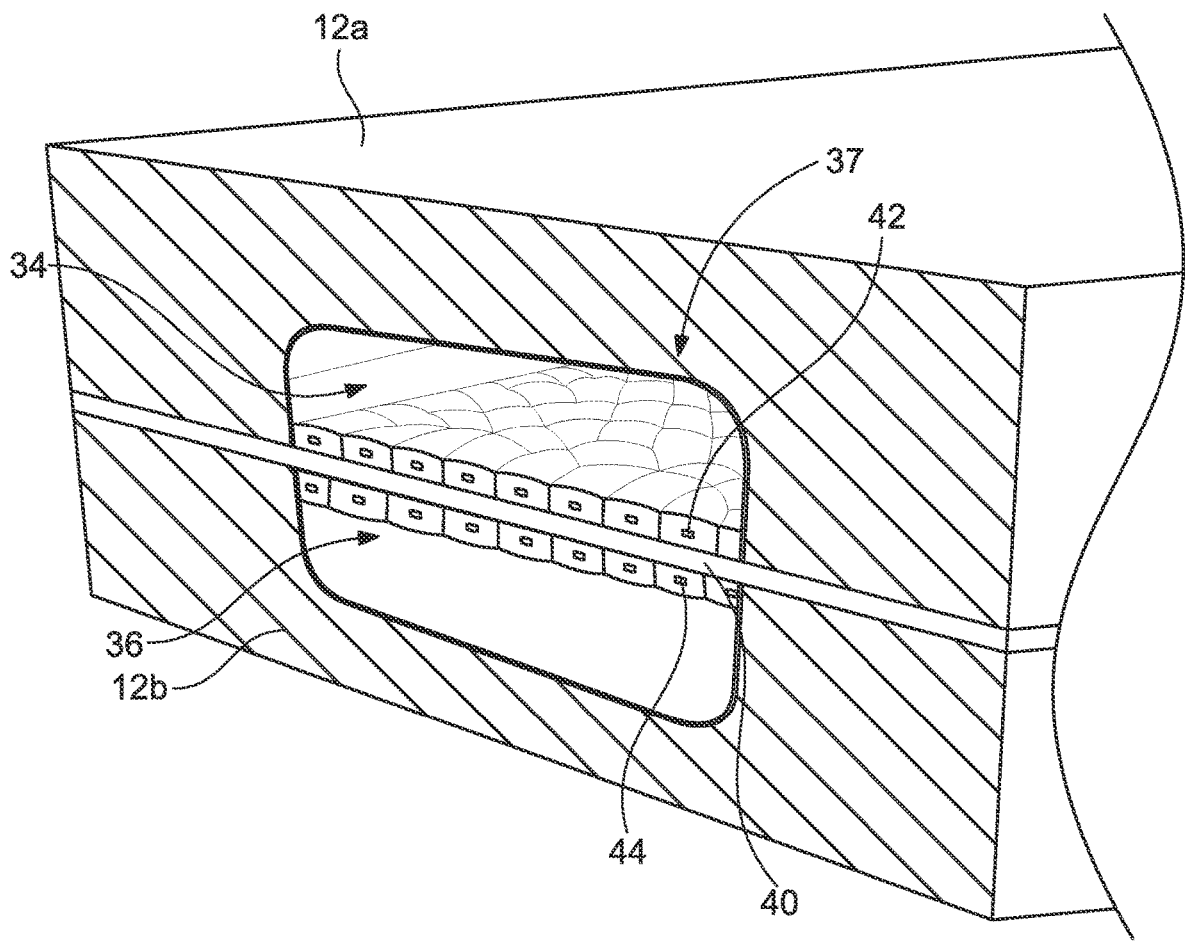
FIG. 2 is a cross-section of the microfluidic device taken along line 2-2 of FIG. 1, illustrating the membrane separating the first microchannel and the second microchannel.

Referring now to FIGS. 1 and 2, one type of a microfluidic device referred to as an organ-on-chip ("OOC") device 10 is illustrated that may be modified (see, e.g., FIGS. 3-5 and 8-12) to include open-top aspects that are described in more detail later in this disclosure. The OOC device 10 includes a body 12 that typically comprises an upper body segment 12a and a lower body segment 12b. The upper body segment 12a and the lower body segment 12b are typically made of a polymeric material, such as PDMS (poly-dimethylsiloxane), polycarbonate, polyethylene terephthalate, polystyrene, polypropylene, cyclo-olefin polymers, polyurethanes, fluoropolymers, styrene derivatives like SEBS (Styrene Ethylene Butylene Styrene), or other polymer materials. The upper body segment 12a, while illustrated with a first fluid inlet 14 and a second fluid inlet 16, can be modified to include an opened region (not shown) to optionally allow the application of a gel layer (not shown) to a membrane 40 and optionally modified to exclude the illustrated first fluid inlet 14 and/or second fluid inlet 16. A first fluid path for a first fluid includes the first fluid inlet 14, a first seeding channel 30, an upper microchannel 34, an exit channel 31, and then the first fluid outlet 24. A second fluid path for a second fluid includes the second fluid inlet 16, a first seeding channel 32, a lower microchannel 36, an outlet channel 33, and then the second fluid outlet 26.

Referring to FIG. 2, a membrane 40 extends between the upper body segment 12a and the lower body segment 12b. The membrane 40 is preferably an inert, polymeric, micromolded membrane having uniformly distributed pores with sizes normally in the range of about 0.1 μm to 20 μm, though other pore sizes are also contemplated. In some aspects, the pore size is in the range of about 0.1 μm to 20 μm. The overall dimensions of the membrane 40 include any size that is compatible with or otherwise based on the dimensions of segments 12a and 12b, such as about 0.05-100 mm (channel width) by about 0.5-300 mm (channel length), though other overall dimensions are also contemplated. In some aspects, the overall dimensions of the membrane are about 1-100 mm (channel width) by about 1-100 mm (channel length). The thickness of the membrane 40 is generally in the range of about 5 μm to about 500 μm, and in some aspects, the thickness is about 20-50 μm. In some aspects, the thickness can be less than 1 μm or greater than 500 μm. It is contemplated that the membrane 40 can be made of PDMS (poly-dimethylsiloxane), polycarbonate, polyethylene terephthalate, styrene derivatives like SEBS (styrene ethylene butylene styrene), fluoropolymers, or other elastomeric or rigid materials. Additionally, the membrane can be made of biological materials such as polylactic acid, collagen, gelatin, cellulose and its derivatives, poly(lactic-co-glycolic acid), or comprise such materials in addition to one or more polymeric materials. The membrane 40 separates an upper chamber from a lower chamber, such as the upper microchannel 34 from the lower microchannel 36 in an active region 37, which includes a bilayer of cells in the illustrated embodiment. In some embodiments, a first cell layer 42 is adhered to a first side of the membrane 40, and in some aspects a second cell layer 44 is adhered to a second side of the membrane 40. The first cell layer 42 may include the same type of cells as the second cell layer 44. Or, the first cell layer 42 may include a different type of cell than the second cell layer 44. And, while a single layer of cells is shown for the first cell layer 42 and the second cell layer 44, either the first cell layer 42, the second cell layer 44, or both may include multiple cell layers or cells in a non-layer structure. Further, while the illustrated embodiment includes a bilayer of cells on the membrane 40, the membrane 40 may include only cells disposed on one of its sides. Furthermore, while the illustrated embodiment includes cells adherent to the membrane, cells on one or both sides may instead be not be adherent to the membrane as drawn; rather, cells may be adherent on the opposing chamber surface or embedded in a substrate. In some embodiments, the said substrate may be a gel.

The OOC device 10 is configured to simulate a biological function that typically includes cellular communication between the first cell layer 42 and the second cell layer 44, as would be experienced in-vivo within organs, tissues, cells, etc. Depending on the application, the membrane 40 is designed to have a porosity to permit the migration of cells, particulates, media, proteins, and/or chemicals between the upper microchannel 34 and the lower microchannel 36. The working fluids within the microchannels 34, 36 may be the same fluid or different fluids. As one example, as device 10 simulating a lung may have air as the fluid in one channel and a fluid simulating blood in the other channel. As another example, when developing the cell layers 42 and 44 on the membrane 40, the working fluids may be a tissue-culturing fluid. It is contemplated that the device offers utility even in the absence of cells on one side of the membrane, as the independent perfusion on either side of the membrane can serve to better simulate mass-transport, shear forces, and other aspects of the biological environment.

In one aspect, the active region 37 defined by the upper and lower microchannels 34, 36 has a length of about 0.1-10 cm, and a width of about 10-2000 μm. The OOC device 10 preferably includes an optical window that permits viewing of the fluids, media, particulates, etc. as they move across the first cell layer 42 and the second cell layer 44. Various image-gathering techniques, such as spectroscopy and microscopy, can be used to quantify and evaluate the effects of the fluid flow in the microchannels 34, 36, as well as cellular behavior and cellular communication through the membrane 40. More details on the OOC device 10 can be found in, for example, U.S. Pat. No. 8,647,861, which is owned by the assignee of the present application and is incorporated by reference in its entirety. Consistent with the disclosure in U.S. Pat. No. 8,647,861, in one preferred aspect, the membrane 40 is capable of stretching and expanding in one or more planes to simulate the physiological effects of expansion and contraction forces that are commonly experienced by cells.

Micro- and mesofluidic devices and membranes can be fabricated from or coated with or otherwise produced from a variety of materials, including plastics, glass, silicones, biological materials (e.g., gelatin, collagen, fibronectin, laminin, Matrigel® (a solubilized basement membrane matrix), chitosan, and others).

Turning now to FIGS. 3 through 12 various exemplary open-top microfluidic devices (e.g., open-top OOC devices) and components are illustrated that can be used for creating gel layers, such as for an open-top skin-on-a-chip device or for creating gel layers for an open-top OOC device for simulating other biological functions.

Figure 3:
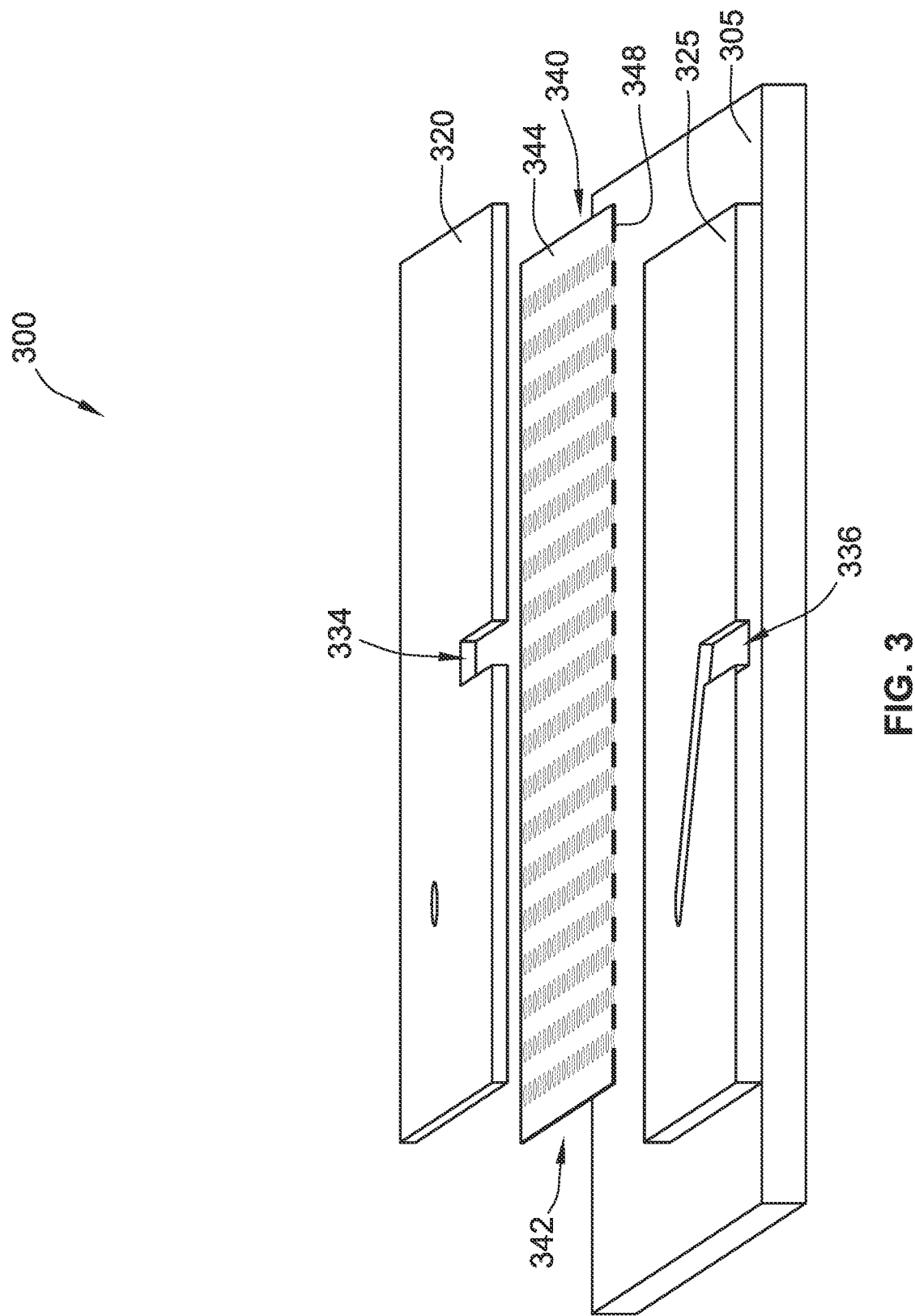
FIG. 3 illustrates an exploded perspective view of an exemplary cross-section through an open-top microfluidic device according to aspects of the present disclosure.

FIG. 3 illustrates an exploded perspective view of a cross-section through an exemplary open-top microfluidic device 300 (e.g., an open-top OOC device). Open-top microfluidic devices, such as an open-top OOC device, that allow access to the top of a chip offer several benefits. Topical treatment, such as for a skin-on-a-chip, can be applied directly through the open top to the tissue of interest. Topical treatments can include, for example, liquid, gas, gel, semi-solid, solid, particulate or aerosol. Furthermore, additional chemical or biological components can be added by means of the open top; as a particular example, additional cell types can be seeded within the open top of the device. Aerosol delivery, such as for a lung-tissue chip, is also contemplated and can be completed through the open top, as well.

The microfluidic device 300 can optionally include a base 305, such as a glass slide, polymeric or metal support or a similar structure, optionally providing an optical window. The base 305 can support a bottom structure 325 of the microfluidic device 300. The bottom structure 325 defines a bottom chamber 336 that is illustrated as a bottom fluidic channel for microfluidic device 300. Above the bottom structure 325 is an interface region 342 that includes a membrane 340 having a top side 344 and a bottom side 348. The bottom side 348 is disposed on the top surface of bottom structure 325 such that bottom side 348 rests above the bottom chamber 336. A top structure 320 is disposed on the top side 344 of membrane 340 and includes an open top chamber, at least a portion of which defines an open region 334 for the open-top microfluidic device (e.g., the open-top chip). When the top structure 320 is disposed on the membrane 340, in may be desirable that all or substantially all of the open region 334 is bounded on the bottom by the top side 344 of the membrane 340. In some aspects, the chamber of the top structure 320 can further include a top fluidic channel (e.g., as illustrated in FIG. 5B). Such a top fluidic channel may permit perfusion of the top chamber, particularly while it is covered by the optional cover. It is contemplated that in some aspects one or both of the bottom fluidic channel and the top fluidic channel are microchannels. It is further contemplated that in some aspects, an optional cover (e.g., not shown but see non-limiting exemplary covers 410 and 510 in FIGS. 4 and 5) is disposed above the open-top structure and may further be in fluid communication with the chamber and the open region 334. The cover may be designed for a one-time application (e.g. by means of bonding it in place) or for subsequent removal.

The chamber is illustrated to include a notch that defines the open region 334 in the open-top structure 320. The primary operation of open region 334 is to allow direct access to the membrane 340 or any matter disposed above it, before, during, and/or after experimentation; such access is not available in earlier closed microfluidic devices for simulating tissues. While previous microfluidic devices, such as OOC, may have allowed for low viscosity fluids to be directed through limited-access channels to a membrane, such as illustrated in FIGS. 1 and 2, the open region 334 of the top chamber in top structure 320 additionally allows for the placement of high viscosity gels, high viscosity fluids, solids, aerosols, and powders on an area of interest for an OOC device (e.g., on the membrane inclusive of a predetermined tissue culture).

Turning now to FIG. 4, an exploded perspective view of a cross-section through an exemplary open-top microfluidic device 400, similar to FIG. 3, is illustrated that further includes a fluidic cover 410. The microfluidic device 400 includes an optional base 405 that supports a bottom structure 425. The bottom structure 425 defines a bottom channel. Above the bottom structure and the bottom channel is an interface region 442 that includes a membrane 440. The membrane 440 is disposed on the bottom structure 425 and above the bottom channel. An open top structure 420 is disposed above the membrane and includes a top chamber with an open region 434, similar to the chamber and open region 334 described for FIG. 3. When the open top structure is disposed on the membrane 440 during assembly of the device 400, it may be desirable that all or substantially all of the open region is bounded along the bottom by the membrane 440.

The fluidic cover 410 may be designed to permit the perfusion of the open region 434 while the cover is present. In some aspects, this configuration provides an advantage compared to enabling the perfusion of the open region 415 by way of a top channel in the top structure 420. One of the benefits of not including a top channel in the top structure 420, is that cells, gel or other materials disposed in the open region 434 are not allowed to leak or spread into the top channel, where they may be undesirable. For example, cells in the top channel will not be allowed to lie away from the active region. In contrast, by disposing the channels in the fluidic cover 410, the benefit is provided of the channels being absent when the cover is removed, which disallows the channels from being similarly filled with cells during seeding, as would happen with channels being disposed in the top structure. The temporary aspect of the fluidic cover provides a removable, and possibly disposable, fluidic component for cell seeding that minimizes or avoids cell seeding throughout the channels.

To minimize "leakage" of a substance of interest placed into the open region into areas where the substance is not desired, different configurations of the open-top microfluidic device are contemplated. For example, the fluidic cover 410 can include a fluidic chamber 415 (which may be a channel or part thereof) that substantially aligns with all or a portion of the open region 434 when the cover is disposed on the top structure 420. The fluidic chamber 415 may optionally be hydraulically connected to one or more inlet ports, which in some aspects may be similar to the ports described for upper body segment 12a in FIGS. 1 and 2. The presence of the fluidic chamber 415 is especially significant where the open region 434 is filled with a gel or other substance that impedes fluid flow. In such a case, the fluidic chamber 415 may be filled or perfused, enabling its contents to fluidically interact with the substance in the open region 434. For example, if the open region 434 holds a gel containing cells, flowing tissue-culture media through the fluidic chamber 415 (or even incubating this media without flow) would allow nutrients and reagents to be delivered to the cells, as well as for waste products to be removed. Through the use of a clamping device, the optional cover of FIG. 3 or the fluidic cover 410 can be mechanically secured to the top structure 420 (e.g., see FIG. 5E) to prevent or minimize leakage of any fluidic substance of interest from the open region 434 of the open-top microfluidic device 400. For example, a spring-loaded clamp can be used to provide compression to a biocompatible polymer that uniformly seals the open region without adhesives. Such sealing can be further improved by including an elastomeric, pliable or soft material in at least one of the cover or top structure 420; one with ordinary skill in the art will appreciate that many forms of gasketing and sealing may be applied here. An advantage of some embodiments that employ clamping is that they facilitate the application, removal and potentially the reapplication of a lid or cover, which may desirably allow access to the open region 415 after it was covered. Allowing access to an open region of a microfluidic device during experimentation can be useful, for example, in (i) the application of topical treatment, aerosol, additional cells or other biological reagents, (ii) change of fluidic (e.g. tissue-culture media), (iii) sampling of fluidic or solid matter, or (iv) imaging using optical or other techniques. The option to reposition the cover or apply a different cover further permits the continued use of the device (e.g. in a biological experiment). Alternatively, the lid or cover may be removed at the end of the device's use to permit sampling that may be destructive, such as taking biopsies or otherwise removing samples, staining, fixing, or imaging.

In some aspects, the cover of FIG. 3 or the fluidic cover 410 can also, or alternatively, be bonded or otherwise disposed onto the top structure 420. For example, for fluidic or gas sealing, an adhesive membrane, laminate, film, or sheet can be used to temporarily or permanently seal the open region at the interface between the top structure that defines the open region and a removable cover. It is also contemplated that biocompatible polymer plugs or pistons can be used to seal off the open region. It is further contemplated that the open region of an open-top microfluidic device can be simply covered (e.g., similar to cell culture plates) with a cover or plate that limits evaporation and improves sterile handling.

In some aspects it is contemplated that the open top structure 420 can be used in an open state, similar to a well, or with a removable cover that may be akin to a flat layer that seals the open top structure 420. An optional configuration in FIG. 4 includes a fluidic chamber 415 with channels that can also introduce fluids into the microfluidic device such as for perfusion or the introduction of other liquids into the system.

As discussed above, the open-top microfluidic device offers a number of advantages. For example, it allows the topical application to a membrane of compounds, including compounds in the form or a gel or powder. The open-top design also allows for aerosol delivery to a simulated tissue directly from the top of the microfluidic device. Furthermore, the open-top configuration allows access to apply simulated wounding to a tissue (e.g., simulate a burn or scratch on the skin or intestine) during the course of testing and the application of a treatment of interest all within the same microfluidic device and as part of the same experimentation cycle. Furthermore, the open-top configurations described herein also allow direct access to the epithelium, and thus, allow the ability to biopsy a sample during testing. Open-top configuration also allow microscopy to be applied during use of a chip, such as the application of electron microscopy, high-magnification imaging methods, and laser-based imaging methods by removing the top cover of the microfluidic device, while optionally maintaining the integrity of the experiment.

In some aspects, it is desirable to simulate one or more functions of lung, as such simulations may be beneficial, for example, in testing compound transport and absorption through the lung, the effect of aerosolized or inhaled compounds, model lung disease, or otherwise observe lung response. In vitro models are known in the art, including for example a lung-on-a-chip microdevice disclosures in U.S. Pat. No. 8,647,861, entitled, "Organ Mimic Device with Microchannels and Methods of Use and Manufacturing Thereof," and the small-airway on-a-chip microdevice disclosures in International Publication No. WO 2015/0138034, entitled, "Low Shear Microfluidic Devices and Methods of Use and Manufacturing Thereof," both of which are hereby incorporated by reference herein in their entireties. A lung model that combines several of desired features in the same model would be beneficial. Desired features include recapitulation of various elements of lung structure and morphology, and the ability to satisfactorily introduce compounds or materials as aerosols, fluidic access (e.g. to emulate blood or air flow), or mechanical forces. For example, a lung model is desirable that minimizes loss of aerosol that can occur in delivery tubing and channels and variation in the aerosol delivery along the length of the channel. According to some aspects of the present disclosure, a lung model that includes one or more of such desired features can be constructed. For example, in one embodiment, a lung module is constructed using an open-top device, such as that illustrated in FIG. 4 (whether employing a fluidic cover 410, the optional cover of FIG. 3, or no cover). Accordingly, lung epithelial cells (e.g. alveolar epithelial cells) can be included or deposited within the open region 415. Optionally, the bottom structure 425 may include endothelial cells, motivated by the presence of similar cells in the vasculature (e.g. capillary bed) of in vivo lung. It is also contemplated that using the various aspects of open-top devices described herein, a lung model may be biologically cultured or operated statically (without continuous flow or with discrete exchanges of some portion of the liquid in the device) or under flow in either fluidic channels disposed in, for example, the bottom structure 425, top structure 420, or cover 410, as well as any combination of these modalities, which may optionally be varied during operation (e.g. begin with discrete fluid exchanges, then introduce flow). In addition, the open region 415 or cell layers within it may be cultured dry, under an air-liquid interface, or submerged, with this mode of culture optionally varied during use. For example, following the example of the lung-on-a-chip and small-airway-on-a-chip devices, it may be desirable to begin lung culture under submerged conditions and transition to an air-liquid interface culture after some maturation period (e.g. ranging without limitation from 1 hour to 7 days, or from 1 day to 14 days). A particular advantage of the various open-top embodiments of the present disclosure is that aerosol may be delivered to the lung cells in the open region, such as open region 415. In one exemplary aspect, while operating the device without the optional cover (or by removing the cover), aerosol can be delivered directly into the open region 415 from above (or substantially above). The aerosol may be generated using any of a variety of aerosol-generation techniques known in the art. Alternatively, an aerosol generation means may be included in a cover that can be placed on top of the open region 415. The cover may be optionally removed or exchanged during use; for example, an aerosol-generating cover may be applied when aerosol is desired and replaced with a fluidic cover 410 when fluidic perfusion is desired. In some embodiments, non-aerosol materials or samples can be applied to cells present in an open region, such as open region 415. This may include materials or samples that are difficult to apply fluidically due to their properties, such as slurries, pastes, solids, or viscous fluids.

Referring now to FIGS. 5A-5F, multiple perspective views, including additional cross-sectional details through an exemplary open-top microfluidic device, are illustrated. The microfluidic device 500 includes a membrane 540, 540' disposed between a bottom structure 525, 525' and a top structure 520, 520'. The bottom structure defines a bottom chamber 536, 536' and the top structure includes a top chamber that defines an open region 534, 534' of the microfluidic device 500. In some embodiments, it is desirable that the open region 534, 534' includes a gel, a porous volume, or another material for testing (e.g., an extracellular matrix or cells embedded in an extracellular matrix). For example, a gel can include gels used in an organ-on-chip model of the skin to house fibroblasts and to support a layer or keratinocytes. In FIG. 5B, a gel layer 550 is introduced into the open region 534 (see FIG. 5A) where the gel layer 550 is bounded on the bottom by membrane 540.

Figure 5A:
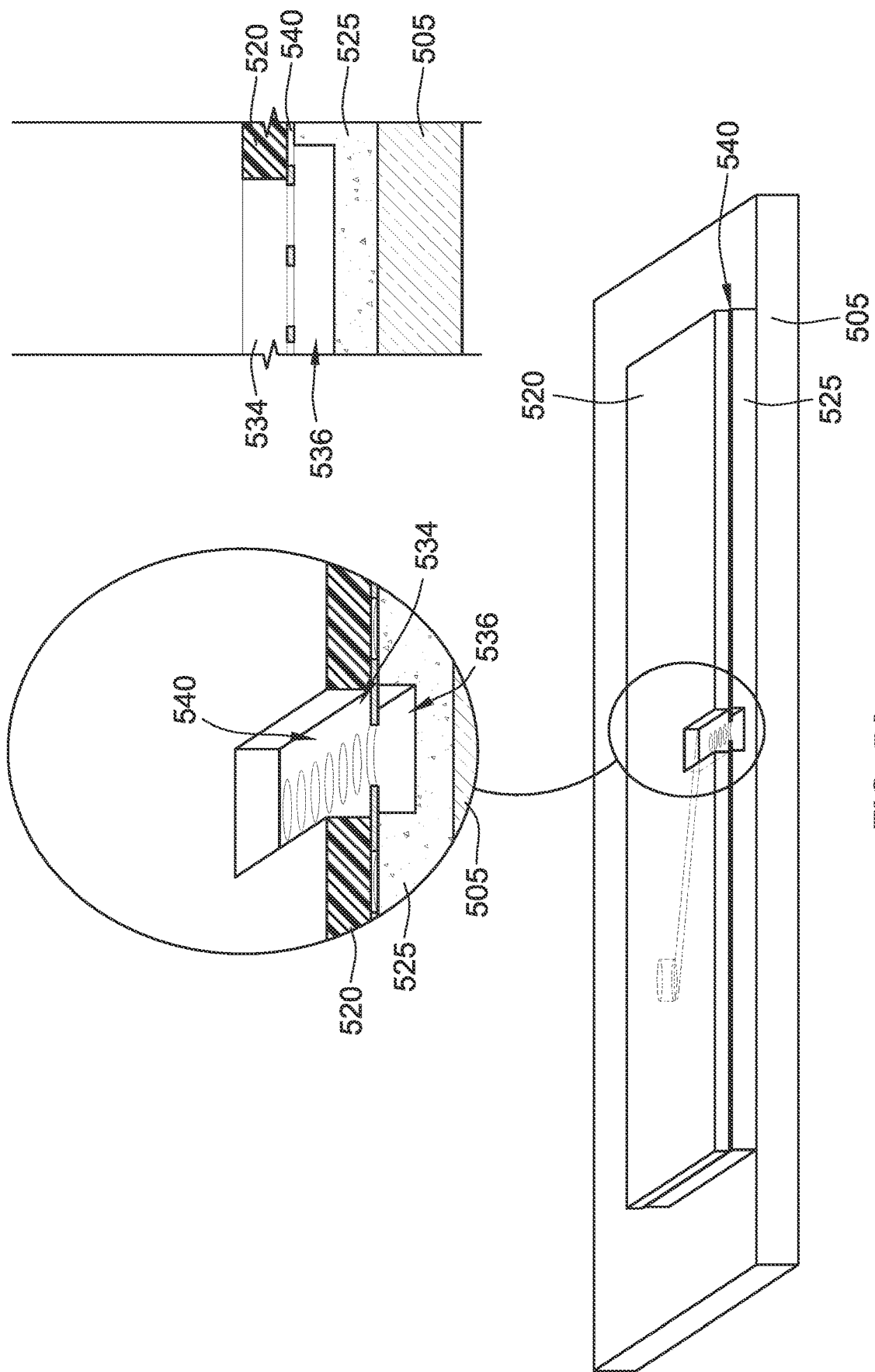
FIG. 5A illustrates a perspective view of an exemplary cross-section through an open-top microfluidic device according to aspects of the present disclosure.
Figure 5B:
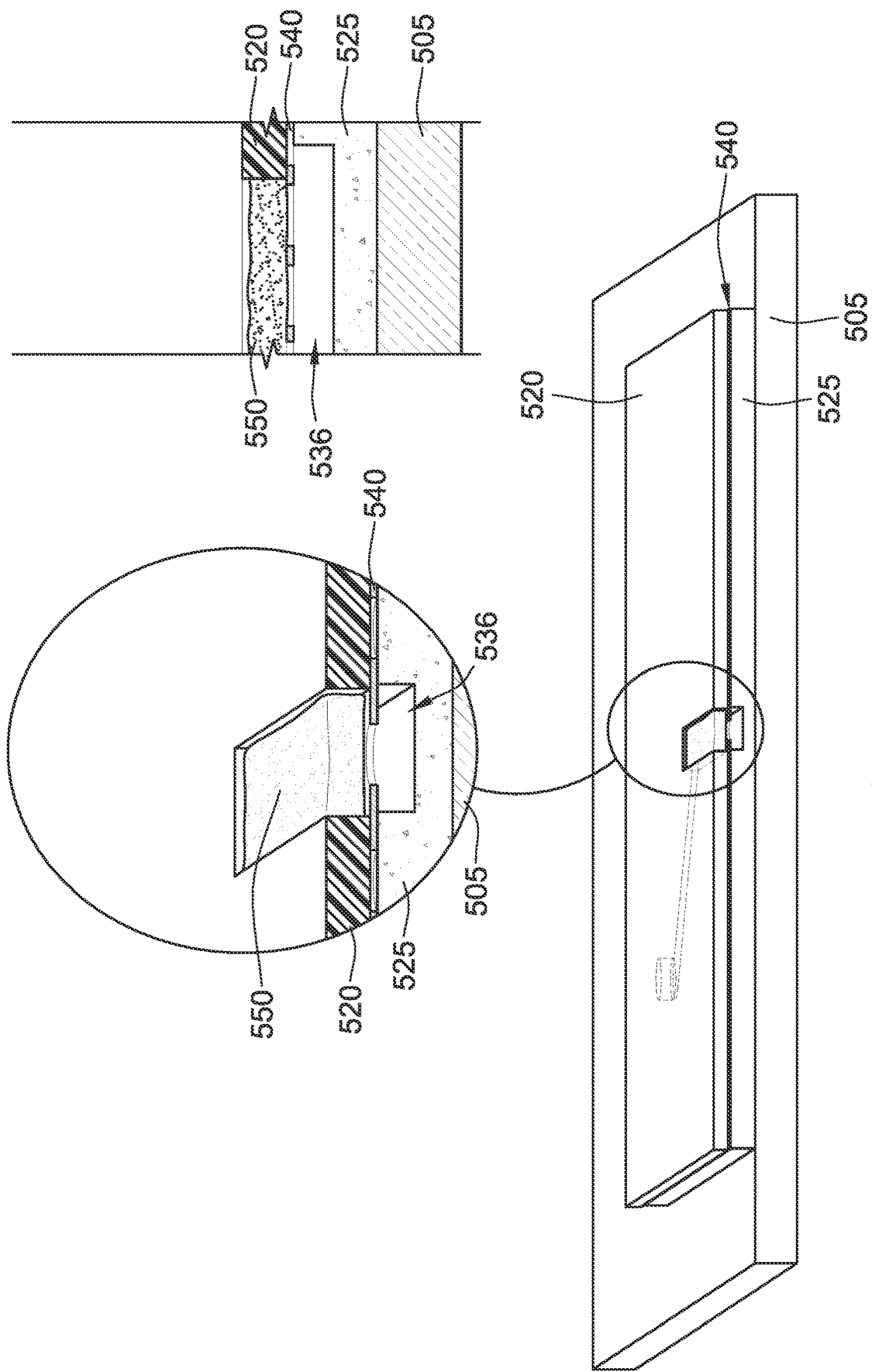
FIG. 5B illustrates a perspective view of the exemplary open-top microfluidic device of FIG. 5A including a gel layer above a membrane layer in an opened region of a top structure according to aspects of the present disclosure.
Figure 5C:
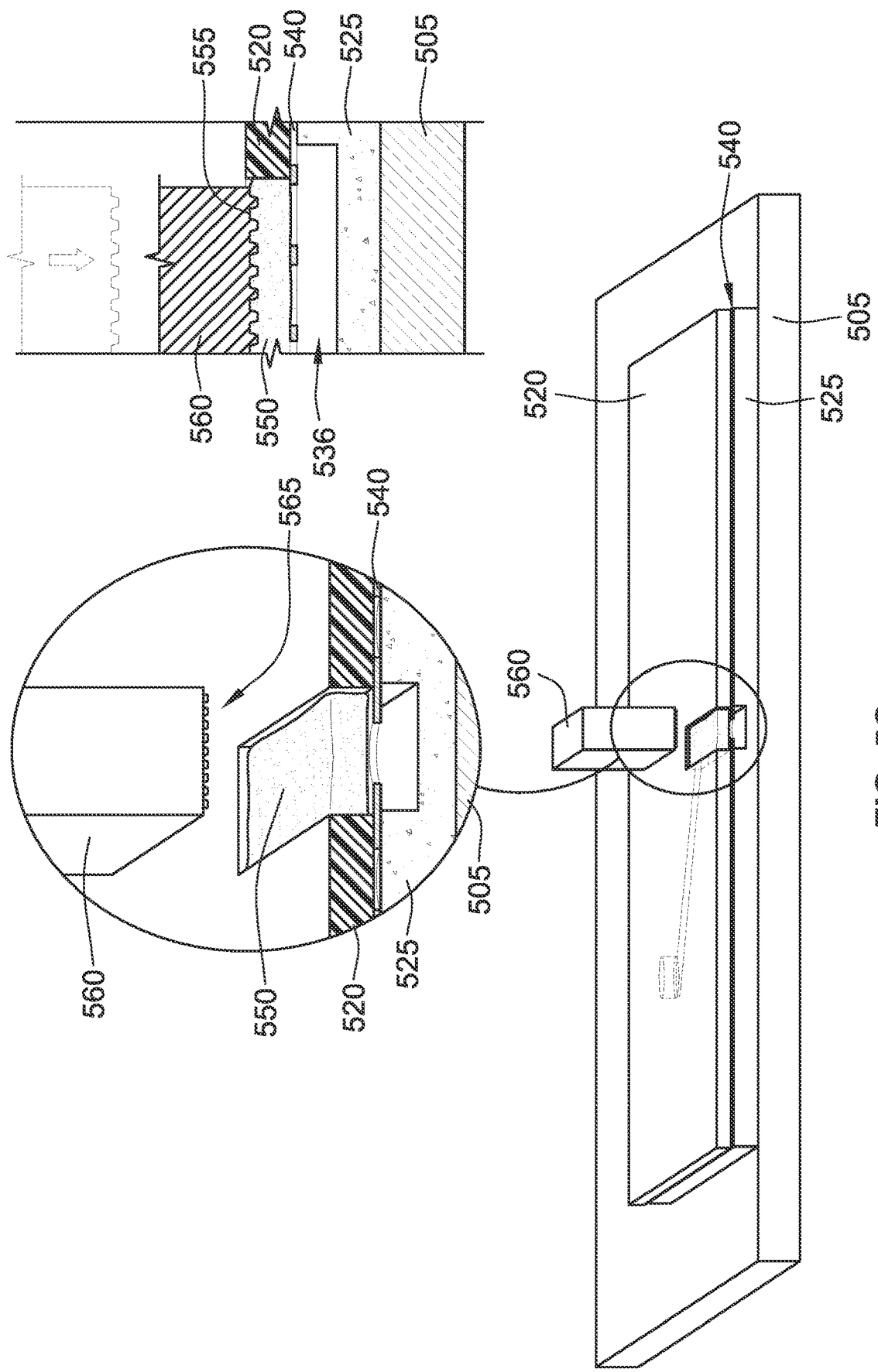
FIG. 5C illustrates a perspective view of the exemplary open-top microfluidic device of FIG. 5B including placement of a plunger stamp into the opened region of the top structure according to aspects of the present disclosure.
Figure 5D:
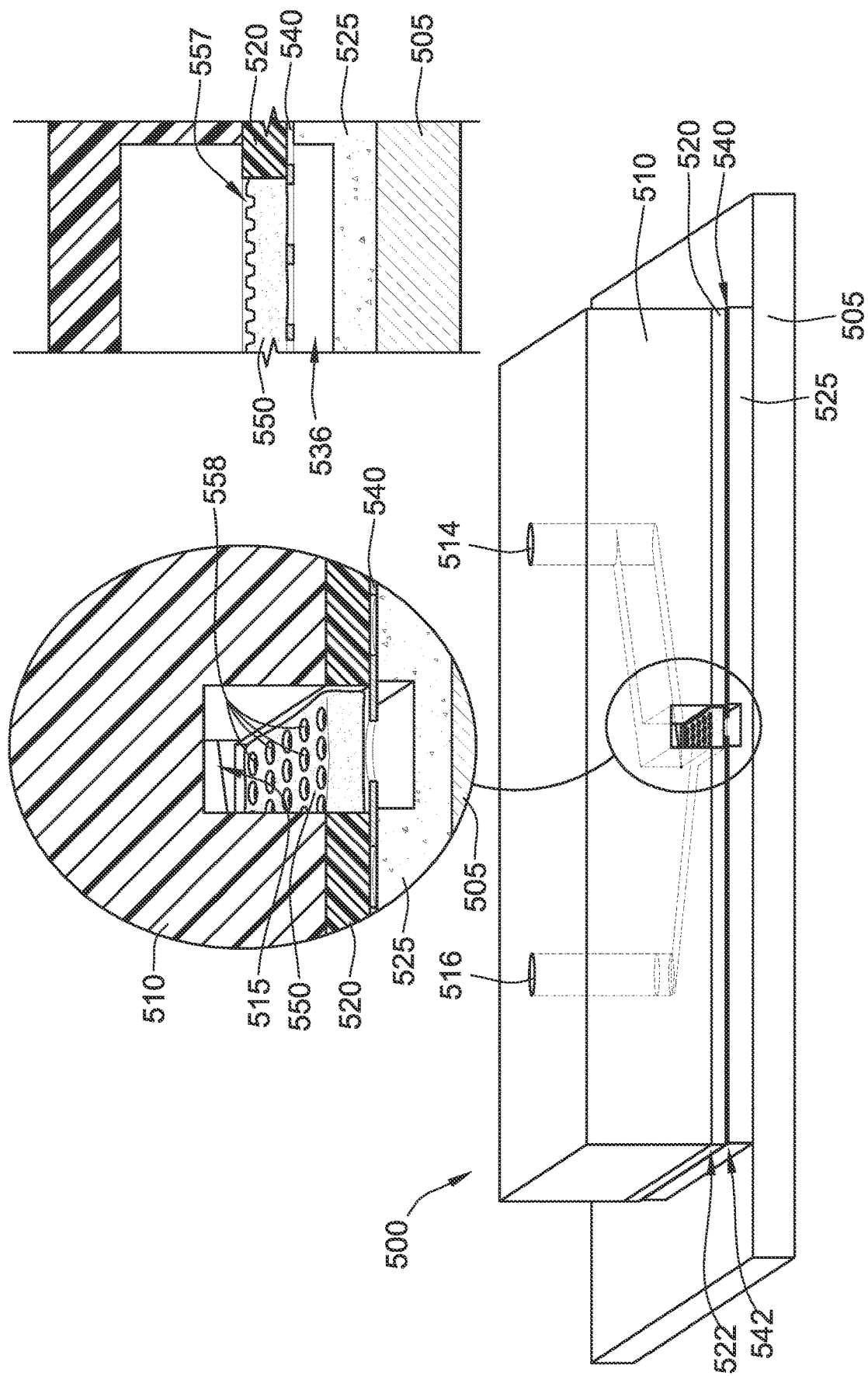
FIG. 5D illustrates a perspective view of the exemplary open-top microfluidic device of FIG. 5C including a patterned gel in the opened region of the top structure and a removable cover disposed above the top structure according to aspects of the present disclosure.

In some embodiments, the gel or porous volume is formed by injecting one or more suitable precursors through one or more fluidic channels included in the top structure 520, 520' (such optional channels are depicted in FIGS. 5A-5C). The one or more precursors can then be treated as desired to form the gel or porous volume (e.g. UV light, chemical treatment, temperature treatment and/or incubation/waiting). Alternatively, the one or more precursors are in a final or near-final form, where no additional active process is applied in order to generate the gel or porous volume. While the approach of injecting the one or more precursors through one or more fluidic channels included in the top structure 520 can be adapted to permit consistent filling with gel or other porous volume, it typically results in the gel or porous volume filling at least part of the said fluidic channels. This may be undesirable in some situations; for example, when dealing with a gel containing cells, it is desirable to limit the cells to the active region, lest they may not receive sufficient nutrient or biochemical cues through the membrane. Alternatively, the one of more precursors can be placed into the top of the open-top microfluidic device via the open region 534, 534'. Such an approach permits alternative embodiments that eliminate or limit spaces into which the precursors may spread (e.g. one may avoid fluidic channels included in the top structure 520, 520' that are in fluidic communication with the open region 534, 534'). In other embodiments, the one or more precursors may be injected into the open region 534, 534' by means of a cover 510 that includes one or more fluidic channels (an example is illustrated in FIG. 5D). Although such embodiments may also result in gel formed in the fluidic channels, the cover 510 can be removed and optionally replaced, removing at least part of the undesired material.

In some embodiments, it is desirable to limit or shape the gel volume or porous volume. For example, in an organ-on-chip model of the skin, it is may be desirable to limit the thickness of a gel layer housing fibroblasts and supporting keratinocytes to a selected thickness. Without limitation, such thickness may be chosen from one or more of the ranges of 10 um to 200 um, 100 um to 1 mm, 0.5 mm to 5 mm, or 1 mm to 10 mm. According to some embodiments, the extent of the gel or porous volume may be limited by a shaping device (e.g., a shaping cover, a plunger with a patterned base) that is present during the introduction or formation of the gel or porous volume. This shaping device may be removed and optionally replaced with a cover once the gel or porous volume has formed. The shaping device may optionally include a chamber to which the gel or porous volume can conform, at least in part. Alternatively, the shaping device may include one or more features that protrude into the open region 534. FIG. 5C illustrates a shaping device with features that protrude into the open region 534, which takes the form of a plunger stamp 560. In some aspects, the shaping device is applied before the introduction of one or more precursors for a gel or porous volume; for example, it could be introduced through fluidic channels present in the top structure 520, a fluidic cover 510 or even in the shaping device itself. In other aspects, the one or more precursors are introduced before the application of the shaping device, whether through fluidic channels in the top structure 520 or fluidic cover 510, or introduced directly into the open region (e.g. using a syringe, pipette or printing process). In such cases, the shaping device may optionally include features (e.g. holes, fluidic channels, cavities) designed to allow the capture of excess precursor. In some embodiments, the shaping device comprises a plurality of layers. For example, the shaping device may include a spacer layer used to define gel height and a flat cover to prevent the gel from passing the spacer's height. All or only a subset of these layers may be removed once the gel or porous volume is defined, with the remaining layers (e.g. spacer layer) potentially remaining during device use or experimentation. In some embodiments, the top structure 520 may be removed after gel or porous volume formation, and can be optionally replaced with a different structure or cover, that may or may not include an open region.

A shaping device, such as plunger stamp 560, can include a patterned surface 565 that creates a pattern in the gel or porous volume at a patterning interface 555. Depending on the properties of the precursor materials (e.g. viscosity of the precursor and its change through curing), the shaping device may be removed before the gel or porous volume have fully formed.

FIG. 5D next illustrates a perspective view of the exemplary open-top microfluidic device of FIG. 5C after a plunger stamp has been removed, including a patterned top surface 557 in the gel layer 550. The patterning includes depressions 558 in the top surface 557 of the gel layer 550. The removable cover 510 can then be placed onto microfluidic device 500 such that chamber 515 aligns with chamber 534. The exemplary cover 510 can optionally include fluidic channels. In the example illustrated, one of the fluidic channels extends from inlet hole 514 to the chamber 515. Another fluidic chamber ends at outlet hole 516 and extends downwardly through the cover 510, through an opening in the membrane 540, and is fluidically connected with chamber 536. The cover 510 may be removable, and once removed it may be optionally reapplied or optionally replaced with a different cover.

Figure 5E:
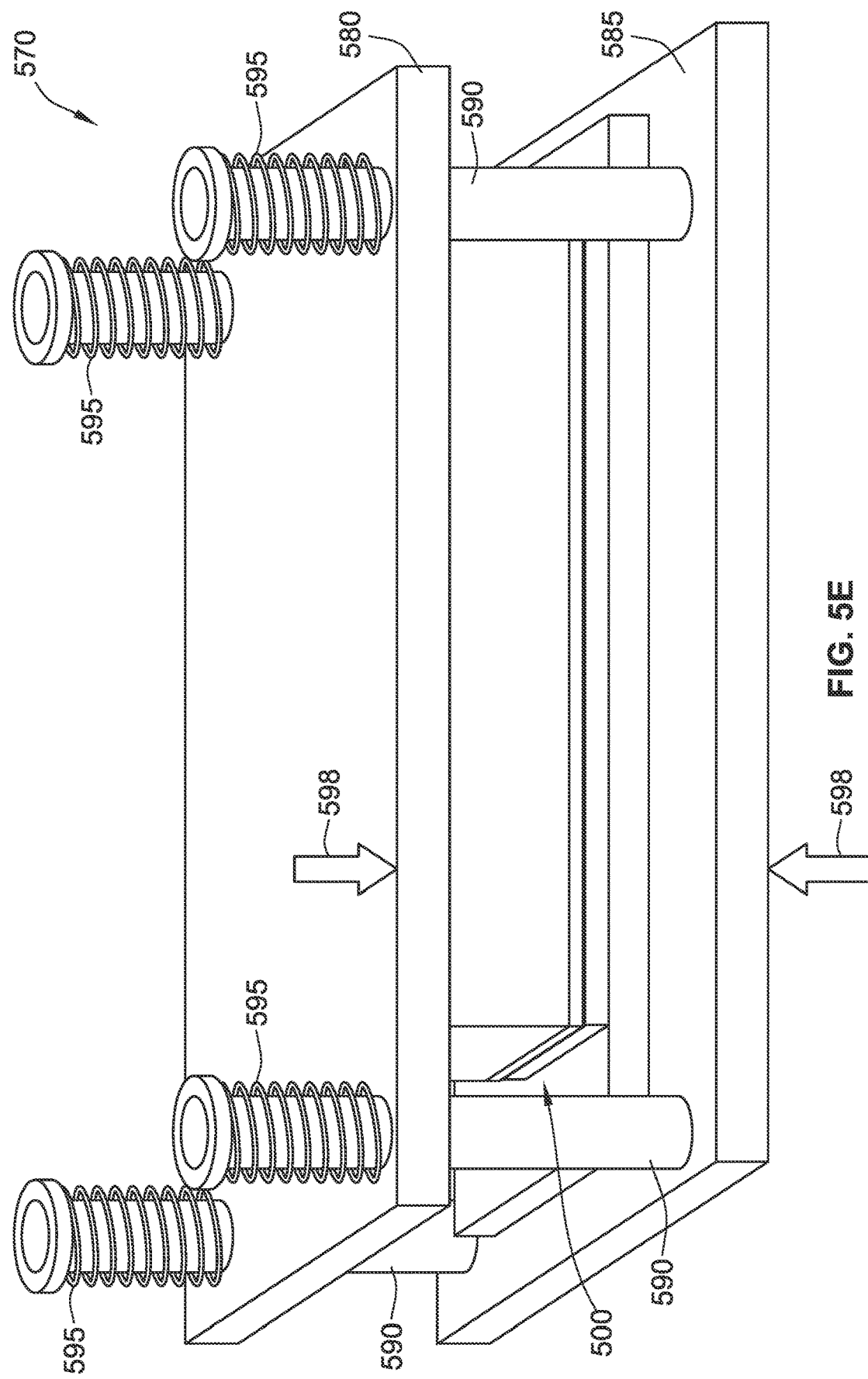
FIG. 5E illustrates a perspective view of the exemplary open-top microfluidic device of FIG. 5D in an exemplary clamping device according to aspects of the present disclosure.

FIG. 5E illustrates the exemplary open-top microfluidic device disposed within an exemplary clamping device 570. A clamping device can be desirable because no glue or bonding is needed to hold the various layers of the microfluidic device together. The clamping device applied to an open-top microfluidic device optionally allows efficient removal of the removable cover during an experiment. The clamping device 570 for the microfluidic device 500 can include an optional base 585 for engaging a first side (e.g., the bottom side) of the microfluidic device 500. In some embodiments, a plurality of elongated posts 590 can extend upwardly from the base 585. A compression plate 580, which may flat or may in some aspects be uneven, is movably coupled to the plurality of elongated posts 590 such that the compression plate 580 is vertically slidable along the posts 590. In some embodiments, the compression plate 580 engages a second side (e.g., the top side) of the microfluidic device 500; in other embodiments, the compression plate 580 retains a cover to the microfluidic device 500. A compression device 580 provides compressive forces (e.g., see arrows 598) generally in a direction along the elongated posts 590. The compression device (e.g., springs 595, elastomers, flextures, etc.) is operatively connected to the compression plate 580 such that the compressive forces (e.g., see arrows 598) create a substantially uniform pressure on the second side (e.g., the top side) of the microfluidic device 500. Clamping device components can be made from different types of materials, including PMMA (e.g., acrylic), thermoplastics, thermoset polymers, other polymer materials, metals, wood, glass, or ceramics. In alternate embodiments, the compressive plate 580 may be held in place using a retention mechanism including one or more of screws, clips, tacky/sticky materials, other retention mechanisms known in the art, or the combination of any of these mechanisms and/or the aforementioned compression device. In some embodiments, the retention mechanism retains the compressive plate 580 with respect to or against the base 585. In alternate embodiments, the retention mechanism retains the compression plate 580 with respect to or against the microfluidic device 500. For example, screws can be used to fasten the compression plate 580 against the microfluidic device 500 with the corresponding threaded holes included in the microfluidic device 500. As another example, the compression plate 580 can include a clip feature (as a retention mechanism) that clips into a suitable receiving feature of the microfluidic device. In some embodiments, the compression plate 580 comprises a cover for an open area included in the microfluidic device 500. In other embodiments, the compression plate 580 retains an additional substrate that comprises a cover for an open area included in the microfluidic device 500.

In some aspects, the compression plate 580 may include at least one access hole (not shown) that substantially aligns with a corresponding fluid port (e.g., inlet hole 514 or outlet hole 516) on the microfluidic device 500 or an optional cover. In some embodiments, the access hole securely holds or comprises a fluid connector. Such a fluidic connector may be beneficial in fluidically interfacing with the microfluidic device 500 or optional cover without necessitating that the connector be included in the microfluidic device 500 or optional cover.

A bottom surface area of the compression plate 500 may be greater or smaller than a top surface area of the microfluidic device 500. In some aspects, the base 585 can have a width such that the compression plate width is greater than the base width. The compression plate 580 can further include finger nubs or tabs (not shown) protruding from a central portion of the compression plate and extending beyond the base such that a compression plate width with the finger nubs is greater than the base width.

In embodiments that include elongated posts 590, it is contemplated that the plurality of elongated posts 590 are substantially parallel and the compression plate 580 includes a plurality of apertures operative to allow an elongated post to pass through a respective aperture. The plurality of elongated posts 590 supports the compression device (e.g., springs 595). The compression device can include at least one spring 595 extending around an outer boundary of at least one of the plurality of elongated posts 590. In some aspects, a compression device comprises two springs that provide a substantial uniform or equalized pressure to a compression plate where the compression plate is a mobile part of the clamping device that moves easily up and down (or along other axes) to allow for easy manipulation of the clamped system. For example, the use of springs in a clamping device can be desirable because springs constants can provide for a wide range of translation distances and forces and are versatile for situations where a clamping device may be positioned upside down for extended periods of time. The compression plate can be modified in area, shape, thickness, or material.

It is contemplated that a maximum compressive force that is provided to the microfluidic device by the clamping device is determined based on the force required to create a fluidic seal between the compression plate 580 or optional cover and the microfluidic device 500 (if such a seal is desired), and the propensity for the collapse of microfluidic channels or chambers within the microfluidic device 500 or optional cover. In some aspects, the compressive forces provided can range from approximately 50 Pa (approximately 0.007 psi) to approximately 400 kPa (approximately 58 psi). In some aspects, the compressive forces provided can range from approximately 5 kPa (0.7 psi) to approximately 200 kPa (29 psi). In some embodiments, it is desirable that the amount of force or pressure applied by a compression plate 580 to a microfluidic device 500 keep a microfluidic device sealed or properly sandwiched between the compression plate 580 and a base 585 while not being so extreme as to cause the collapse of the microfluidic channels or to prevent desired gas exchange.

A glass slide or other transparent window (e.g. made of PMMA, polycarbonate, sapphire) can be integrated into the clamp device to provide a rigid support for the microfluidic device which improves pressure distribution for flexible devices (such as those made from PDMS silicone) while enabling good optical access for macroscopic, visual, or microscopic imaging that may be desirable through viewing portions of the clamp system.

It is contemplated that the described clamping device can facilitate the use or positioning of the device in an upside down position. This can be a particularly desirable feature during cell seeding of the underside of a chip membrane, commonly done during OOC co-culture.

A compression device for the clamping device 500 can include alternatives to springs or other aforementioned compression devices or retention mechanisms. For example, hydraulic or pneumatic compression systems are contemplated. It is also contemplated that for rigid microfluidic devices compliant gaskets can be used. For example, the clamping device 500 can be fitted with a compliant gasket that has a level of springiness to it rather than a spring itself. The compliant gasket materials would create an interface between the compression plate 580 and the microfluidic device 500 or between an optional cover and the microfluidic device 500. It is also contemplated that in some aspects a compression device can utilize geometric shapes, such as cantilevered beams, as part of the device design to provide compressive force resulting from the case material flexure or compression. In some aspects, the compressive force can also be provided with magnetic or electromagnetic systems.

Figure 5F:
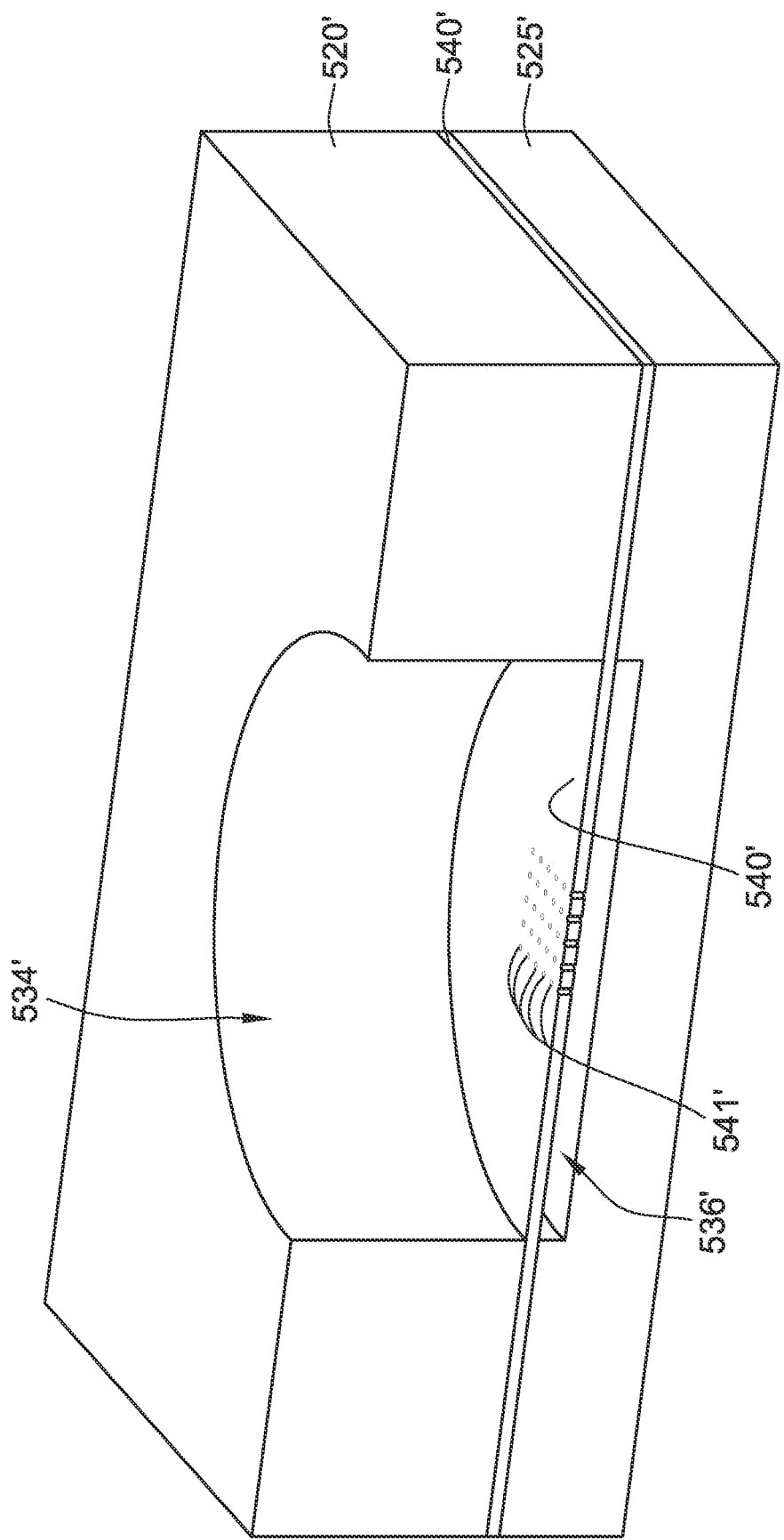
FIG. 5F illustrates a perspective view of an alternative exemplary cross-section through an open-top microfluidic device according to aspects of the present disclosure.

FIG. 5F illustrates a perspective view of an alternative exemplary cross-section through an open-top microfluidic device, similar to device 500, with a bottom chamber 536' and open region 534' of a top chamber that are generally circular from a top or bottom view perspective. Other aspects can include an oval or football shape for the open region and/or chambers. Another exemplary feature includes a membrane 540' disposed between the bottom structure 525' and the top structure 520, where the bottom structure defines the bottom chamber 536' and the top structure defines the open region 534' of the top chamber. The illustrated membrane 540' limits passage between the channels (e.g., the open region and the bottom chamber) to select locations 541' that in some aspects comprise less than the entire surface area of the membrane within the open region 534' and bottom chamber 536'. The select locations 541' may include laser cut holes for passage of a gel, a porous volume, or another material (e.g., an extracellular matrix or cells embedded in an extracellular matrix) that has been disposed in the open region for testing. In some aspects, the select locations 541' may include holes fabricated through a molding, ablation, etching, or other process. The holes at the select locations 541' are fabricated into a pattern that may include holes of different diameters and spacings that are defined within the membrane separating the open region and bottom chamber of the open-top microfluidic device. A patterned approach can be beneficial for (i) optimizing the design of a microfluidic device to a specific tissue application, (ii) producing multiple microenvironments for tissue, organ, or microbiome development, and/or (iii) improving a sensor or electrode function by limiting the region that can be sensed (e.g., a sensor or actuator located in a cover).

In some aspects, an open-top microfluidic device allows for the direct deposition of a matrix, for example a gel or a porous volume or a biodegradable polyester such as polycapolactone, into the open region or open portion of an open-top microfluidic device. For example, a gel-forming solution or precursor can be placed in a mold that is separate from the microfluidic device. The mold can approximate the shape of the chamber or open region into which the gel volume will be disposed for a desired experiment. Similar to setting a gel layer directly into the microfluidic device (see FIGS. 5C-5D), a plunger stamp is placed into the gel solution in the mold such that a bottom surface of the plunger stamp is in contact with the gel solution in the mold. The bottom surface of the plunger stamp includes the pattern of features for imprinting into the gel solution. After the gel solution has at least partially solidified, the plunger stamp is then removed from the gel solution, thereby creating a patterned gel to simulate a tissue microstructure. Once the gel has solidified to the point where the gel will not break apart or otherwise separate, the patterned gel can be removed from the mold and be inserted into the similarly shaped open region of the actual microfluidic device to be used for experimentation. Alternatively or in combination, a suitably shaped volume or gel or porous volume can be cut to size, 3D printed or aggregated from smaller volumes, then disposed into the open region. Further, the gel or porous volume can be 3D printed directly into the open region. In another related aspect, a matrix (e.g., gel or porous volume) such as one formed as described for FIGS. 5C-5D, can also be easily extracted (whether whole or in part) from the top structure of an open-top microfluidic device, which provides benefits by overcoming the problem of staining and high-resolution imaging without having to stain an entire chip or having to reconstruct cell-monolayers. The removal or insertion of a gel, porous material and/or biological sample (e.g. biopsy, blood) to or from the open region of an open-top microfluidic device is also desirable because it can allow access for testing of the subject tissue sample in the microfluidic device and/or then the subsequent removal of the sample from the OOC device, which can then be used for other applications (e.g., for implantation into a patient; additional analysis in another device). In an alternative embodiment, the gel or gel containing cells or tissue can be patterned following culture of cells in the gel material.

In some aspects of a microfluidic device, it is desirable to include a cover that comprises sensors or actuators. For example, a cover can comprise one or more electrodes that can be used for measurement of electrical excitation. In some aspects, such as where the device comprises a membrane (e.g., membrane 540), the one or more electrodes can be used to perform a measurement of trans-epithelial electrical resistance (TEER) for the membrane. It may also be desirable to include one or more electrodes on the opposite side of the membrane 540. In some aspects, the electrodes can be included in a bottom structure (e.g., bottom structure 525). In some aspects, the bottom structure can be an open bottom with bottom electrodes included on a bottom cover that can be brought into contact with the bottom structure. The bottom cover may support any of the features or variations discussed herein in the context of a top cover, including, for example, removability, fluidic channels, multiple layers, clamping features, etc.

In some aspects, it is desirable to simulate one or more functions of skin, for example, in testing compound transport and absorption through the skin, the effect of topical treatments on skin aging or healing, modeling skin disease, or observing skin response such as damage or sensitization. While in vitro skin models are known, such as living skin equivalent (LSE), a skin model that combines several features in the same model would is desirable. For example, desirable features can include recapitulation of various elements of skin structure and morphology, topical access, fluidic access (e.g. to emulate blood flow), or mechanical forces. According to some aspects of the present disclosure, a skin model that includes one or more of such desired features can be constructed. In one exemplary aspect, the skin model is constructed using the open-top device illustrated in FIG. 5D. Accordingly, a gel layer 550, which may be considered to correspond to the skin's dermal layer, is present in or introduced into (e.g. using any of the aforementioned methods) the open region 534, 534'. Optionally, the gel layer 550 (or other matrix) may include embedded fibroblasts or related cells, motivated by the presence of similar cells in the dermal layer of in vivo skin. Furthermore, the gel layer 550 is topped by keratinocytes, which are a primary cell type of the skin. The keratinocytes may, for example, be deposited on top of the gel layer 550 (which can be done, for example, directly through the open top or introduced fluidically through channels present in the top structure 520, 520' or cover 510) or present in the gel or other device component and allowed to biologically mature or develop into a cell layer at the top of the gel layer 550. Optionally, the bottom structure 525, 525' includes endothelial cells, motivated by the presence of similar cells in the vasculature (e.g. capillary bed) of in vivo skin. Using various aspects of the open-top device described herein, the resulting skin model may be biologically cultured or operated statically (without continuous flow or with discrete exchanges of some portion of the liquid in the device) or under flow in either fluidic channels disposed in the bottom structure 525, 525', top structure 520, 520', or cover 510, as well as any combination of these modalities, which may optionally be varied during operation (e.g. begin with discrete fluid exchanges, then introduce flow). In addition, the open region 534 or cell layers within the open-top microfluidic device may be cultured dry, under an air-liquid interface, or submerged, with this mode of culture optionally varied during use. For example, following the example of prior skin models such as the LSE, it may be desirable to begin keratinocyte culture under submerged conditions and transition to an air-liquid interface culture after some maturation period (e.g. ranging without limitation from 1 hour to 3 days, or from 1 day to 14 days). The gel layer 550 may comprise a biological or synthetic gel or other porous volume, including for example, collagen I, collagen IV, fibronectin, elastin, laminin, gelatin, polyacrylamide, alginate, or Matrigel® (a solubilized basement membrane matrix). Collagen I in particular has been used by prior skin models, whereas it is known that elastin is present in in vivo skin, motivating its use in the disclosed in vitro model.

In some aspects, it can be similarly desirable to simulate one or more functions of the intestine, for example, in testing compound transport and absorption through the intestine or its parts, the effect of treatments on intestine health or healing, modeling intestinal disease, or observing intestinal response such as damage or sensitization. In vitro intestinal models are known in the art, including for example transwell-based systems or the gut-on-a-chip microdevice disclosures in U.S. Patent Publication No. 2014/0038279, entitled "Cell Culture System," which is incorporated by reference herein in its entirety. In some aspects, it is desirable construct an intestinal model that combines several of the desired features in the same model, including recapitulation of various elements of intestinal structure and morphology, fluidic access (e.g. to emulate luminal transport or blood flow), or mechanical forces. According to some aspects of the present disclosure, an intestine model that includes one or more of such desired features can be constructed. In one exemplary aspect, the intestine model is constructed using the open-top device illustrated in FIG. 5D. Accordingly, a gel layer 550, is present in or introduced into (e.g. using any of the aforementioned methods) the open region 534, 534'. Furthermore, the gel layer 550 is topped by intestinal epithelial cells. The intestinal epithelial cells may, for example, be deposited on top of the gel layer 550 (which can be done, for example, directly through the open top or introduced fluidically through channels present in the top structure 520, 520' or cover 510) or be present in the gel or other device component and allowed to biologically mature or develop into a cell layer at the top of the gel layer 550. Optionally, the bottom structure 525, 525' includes endothelial cells, motivated by the presence of similar cells in the vasculature (e.g. capillary bed) of in vivo intestines. Optionally, the gel layer 550 includes cells, for example, smooth muscle cells, neuronal cells, lymphatic cells or other cells types, cultures within the gel layer 550. Using various aspects of the open-top device described herein, the resulting model may be biologically cultured or operated statically (without continuous flow or with discrete exchanges of some portion of the liquid in the device) or under flow in either fluidic channels disposed in the bottom structure 525, 525', top structure 520, 520', or cover 510, as well as any combination of these modalities, which may optionally be varied during operation (e.g. begin with discrete fluid exchanges, then introduce flow). Although cells of the intestine are typically cultured submerged, the open-top device also permits the open region 534 or cell layers within it to be cultured dry or under an air-liquid interface, to simulate intestinal gas or various pathologies (e.g. swallowed air or gas presence with irritable bowel syndrome or lactose intolerance), or cultured with highly viscous or solid particulate material (e.g., food, fecal matter, etc.) with the mode of culture optionally varied during use. The gel layer 550 may comprise a biological or synthetic gel or porous volume, including for example, collagen I, collagen IV, fibronectin, elastin, laminin, gelatin, polyacrylamide, alginate, or Matrigel® (a solubilized basement membrane matrix).

It some aspects, it can be similarly desirable to simulate one or more functions of the small airway, for example, in testing compound transport and absorption through the airway or its parts, the effect of treatments on airway health or healing, modeling airway disease, or observing airway response such as damage or sensitization. In vitro small airway models are known in the art, including for example the small-airway on-a-chip microdevice disclosures in International Publication No. WO 2015/0138034, entitled, "Low Shear Microfluidic Devices and Methods of Use and Manufacturing Thereof," which is hereby incorporated by reference herein in its entirety. According to some aspects of the present disclosure, a small-airway model can be constructed to include one or more desired features, including for example fluidic access to airway and vasculature, several of the differentiated cell types found in the in vivo airway (e.g. ciliated cells, mucus-producing cells), and immune response. In one exemplary aspect, the small-airway model is constructed using the open-top device illustrated in FIG. 5D. Accordingly, a gel layer 550, is present in or introduced into (e.g. using any of the aforementioned methods) the open region 534, 534'. Furthermore, the gel layer 550 is topped by small-airway epithelial cells. The small-airway epithelial cells may, for example, be deposited on top of the gel layer 550 (which can be done, for example, directly through the open top or introduced fluidically through channels present in the top structure 520, 520' or cover 510). Optionally, the bottom structure 525, 525' includes endothelial cells, motivated by the presence of similar cells in the vasculature (e.g. capillary bed) of in vivo airway. Using various aspects of the open-top device described herein, the resulting model may be biologically cultured or operated statically (without continuous flow or with discrete exchanges of some portion of the liquid in the device) or under flow in either fluidic channels disposed in the bottom structure 525, 525', top structure 520, 520', or cover 510, as well as any combination of these modalities, which may optionally be varied during operation (e.g. begin with discrete fluid exchanges, then introduce flow). In addition, the open region 534 or cell layers within it may be cultured dry, under an air-liquid interface, or submerged, with this mode of culture optionally varied during use. The gel layer 550 may comprise a biological or synthetic gel or porous volume, including for example, collagen I, collagen IV, fibronectin, elastin, laminin, gelatin, polyacrylamide, alginate, or Matrigel® (a solubilized basement membrane matrix).

In some aspects, it is desirable to provide mechanical strain or force to at least a portion of the fluidic device. In particular, it may be desirable to apply mechanical force to at least some cells present within the fluidic device. According to some aspects, a mechanical force is applied to at least one portion of an open-top device by incorporating an actuation mechanism. In some embodiments, this actuation mechanism can include one or more operational channels, similar to ones described by U.S. Pat. No. 8,647,861, which is hereby incorporated by reference herein in its entirety. Such operational channels can be evacuated or pressurized to cause the application of force to a portion of the device, for example, a membrane separating a top and bottom fluidic channels. In this example, any cells present on top or below the membrane may experience the mechanical force, leading to a potential biological effect. In some aspects, an open-top device is included in a system that additionally includes an actuation mechanism. In some aspects, this actuation mechanism comprises a system for mechanically engaging the open-top device and a system for applying a stretch or compression force. A number of examples of actuation systems included in a fluidic device or in systems that include a fluidic device are described by International Publication No. WO 2015/138032, entitled "Organomimetic Devices and Methods of Use and Manufacturing Thereof", which is hereby incorporated by reference herein in its entirety. In one exemplary aspect, a system comprises an open-top device, a mechanical engaging device including one or more clamps or pins, and a mechanical actuation device including one or more electrical motors or pneumatic cylinders. According to one method to employ such a system, the open-top device is engaged with the mechanical engaging mechanism (e.g. by slipping the one or more pins into corresponding holes included in the open-top device), and actuating said one or more electrical motors or pneumatic cylinders to apply a cyclical mechanical force on at least part of the open-top device.

Figure 6:
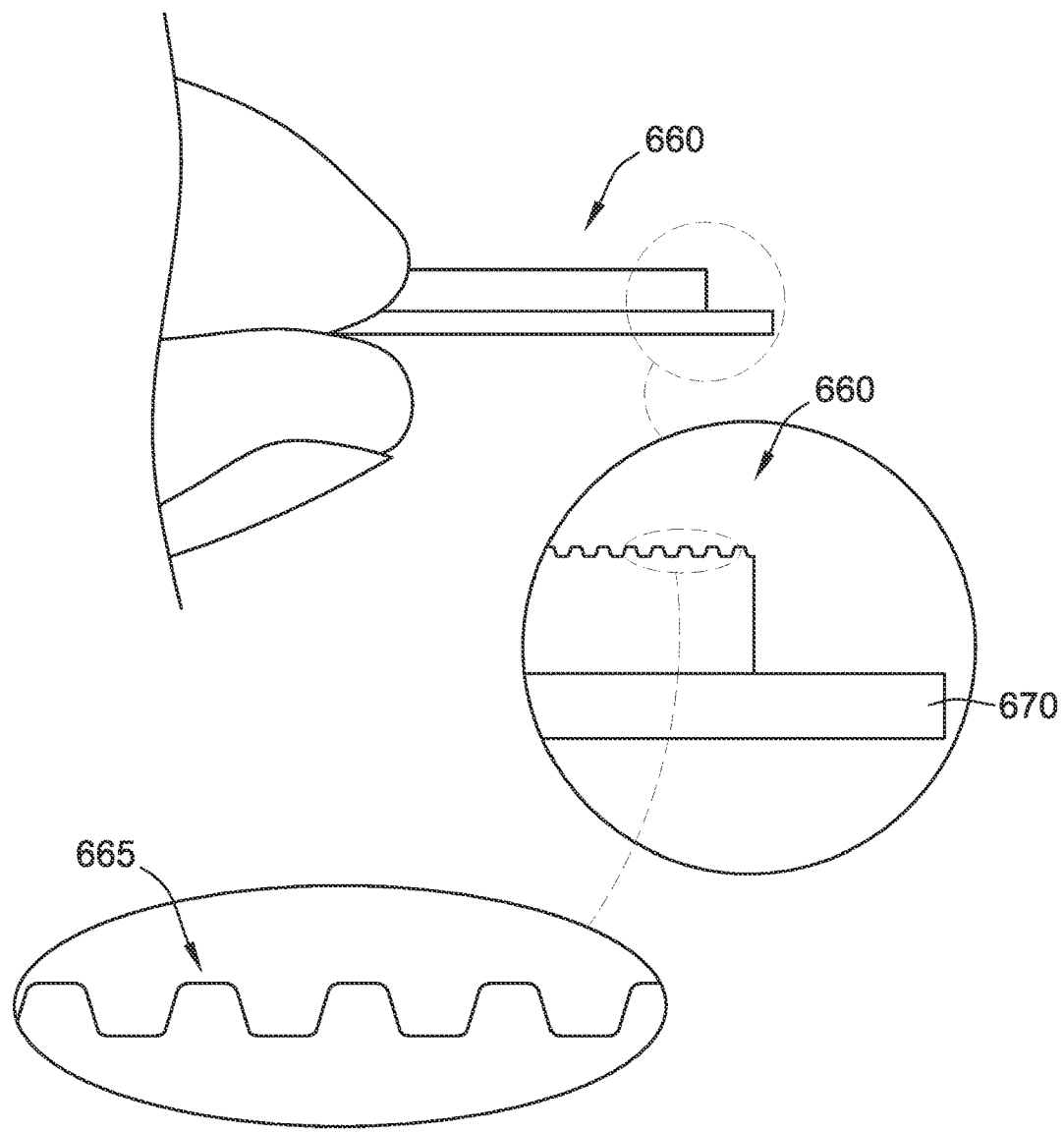
FIG. 6 illustrates an exemplary plunger stamp with a patterned surface according to aspects of the present disclosure.

Turning now to FIG. 6, another exemplary shaping device (in this case a plunger stamp 660) with a textured bottom surface 665 is illustrated for simulating biological conditions in an open-top microfluidic device (e.g., an open-top OOC device). The plunger stamp 660 can be used in a similar manner as illustrated in FIGS. 5C and 5D. Plunger stamps can also be used to create gel layers of a defined thickness in the open region of an open-top microfluidic device. This can be particularly beneficial where a separate section or layer may be needed to introduce a dermal equivalent layer, such as a collagen plus a fibroblast. A plunger stamp can also be beneficial for skin development in, for example, an open-top OOC device, by allowing the creation of a thick gel layer (e.g., about 50 micrometers to about 10 millimeter thick, about 100 micrometers to about 1 millimeter thick), such as for an in vivo skin section. The plunger stamp can also be used in applications where cells are embedded into a system, such as an ECM with the introduction of cells into the matrix. Application of a plunger stamp to a gel in an open region of an open-top microfluidic device also allows for the embedding of fibroblasts into the gel layer.

Patterned surfaces created with a shaping device (e.g. plunger stamp) can provide for more accurate simulation of tissue or organ characteristics, such as for skin tissue, small-airway tissue and intestine. For example, a gel layer for a skin model can be formed to be undulating, with the undulations mimicking features of in vivo papillae or rete peg structures. Such structures are hallmarks of in vivo skin and can vary with skin health and age. Accordingly, the ability to form and control structures in the open-top chip that mimic the in vivo structures is a beneficial aspect of the disclosed open-top microfluidic systems. As a further example, patterning using a shaping device (e.g. plunger stamp) can be used to recreate structure in an intestinal model that mimic intestinal villi. Villi are understood to be an important aspect of the in vivo intestine, as amongst other things because they correspond to a villus-crypt axis of cell differentiation. The ability to controllably form structures that mimic villi in an intestinal model is another beneficial aspect of the disclosed open-top microfluidic systems.

The type of pattern formed on the gel or porous volume may also determine if desired cell types will form in or on the said gel or porous volume. For example, adult keratinocyte cells may not differentiate and may die if the geometry of the gel does not sufficiently simulate the cells' native environment. Using a patterned shaping device (e.g. patterned plunger stamp) that allows the imprinting of specific and sophisticated patterns (e.g., patterning and/or geometries simulating the native environment for cells being cultured) into the gel or porous volume surface, a desirable micro-environment can be created that may allow for cell survival and cell differentiation.

Figure 7:
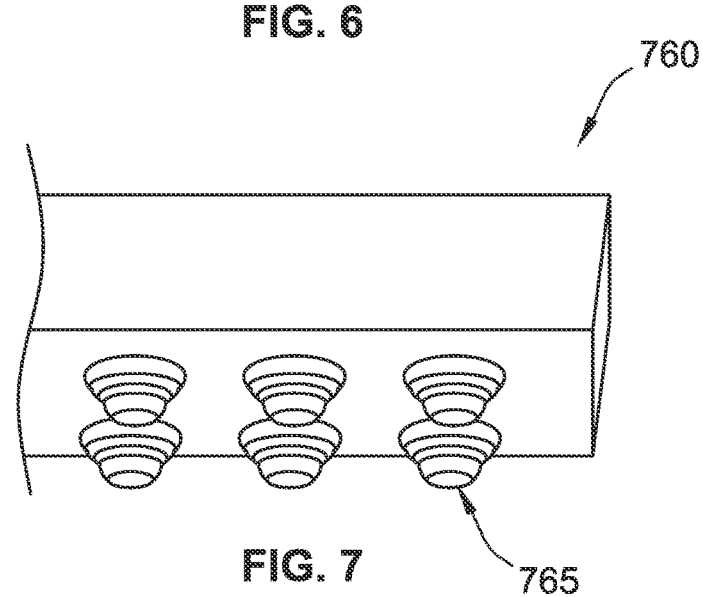
FIG. 7 illustrates an exemplary pattern for a plunger stamp according to aspects of the present disclosure.

Turning now to FIG. 7, an exemplary pattern for a plunger stamp 760 is illustrated. The plunger stamp 760 includes a patterned bottom surface with a plurality of simulated papillae structures 765 that mimic the papillae structure of the dermis, which when imprinted into the surface of a gel layer can be useful for differentiation of an adult skin equivalent.

In some aspects, the gel layer is first placed into the open region of the top structure of a microfluidic device or placed into a mold (e.g., simulating the open region) followed by the stamping of the gel surface with the plunger stamp. In other aspects, the plunger stamp is first inserted into the open region to a predetermined desired based on a desired gel layer thickness and a pre-polymerized gel with a lower-viscosity than in its final cured form is placed or allowed to flow into the open region confined by the plunger stamp, the membrane, and the sides of the open region. The plunger stamp is dimensioned such that there are sufficient tolerances (e.g., gaps) between the side of the plunger stamp and the side walls of the open region (e.g., channel) so that the gel does no ooze or leak up the side of the open region when the pre-polymerized gel is imprinted with the patterned surface of the plunger stamp.

Figure 8A:
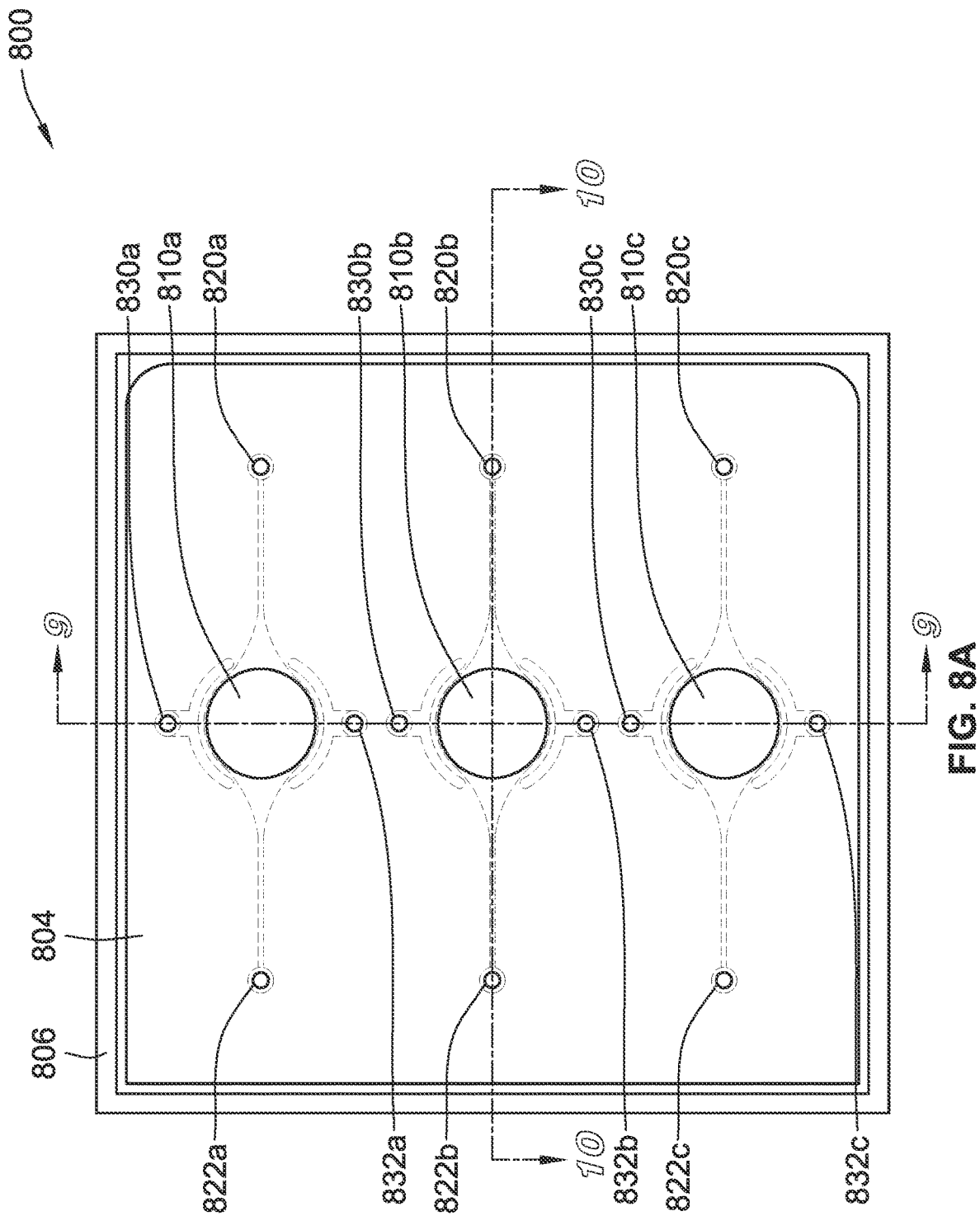
FIG. 8A illustrates a top view of an exemplary stretchable open-top microfluidic device according to aspects of the present disclosure.
Figure 8B:
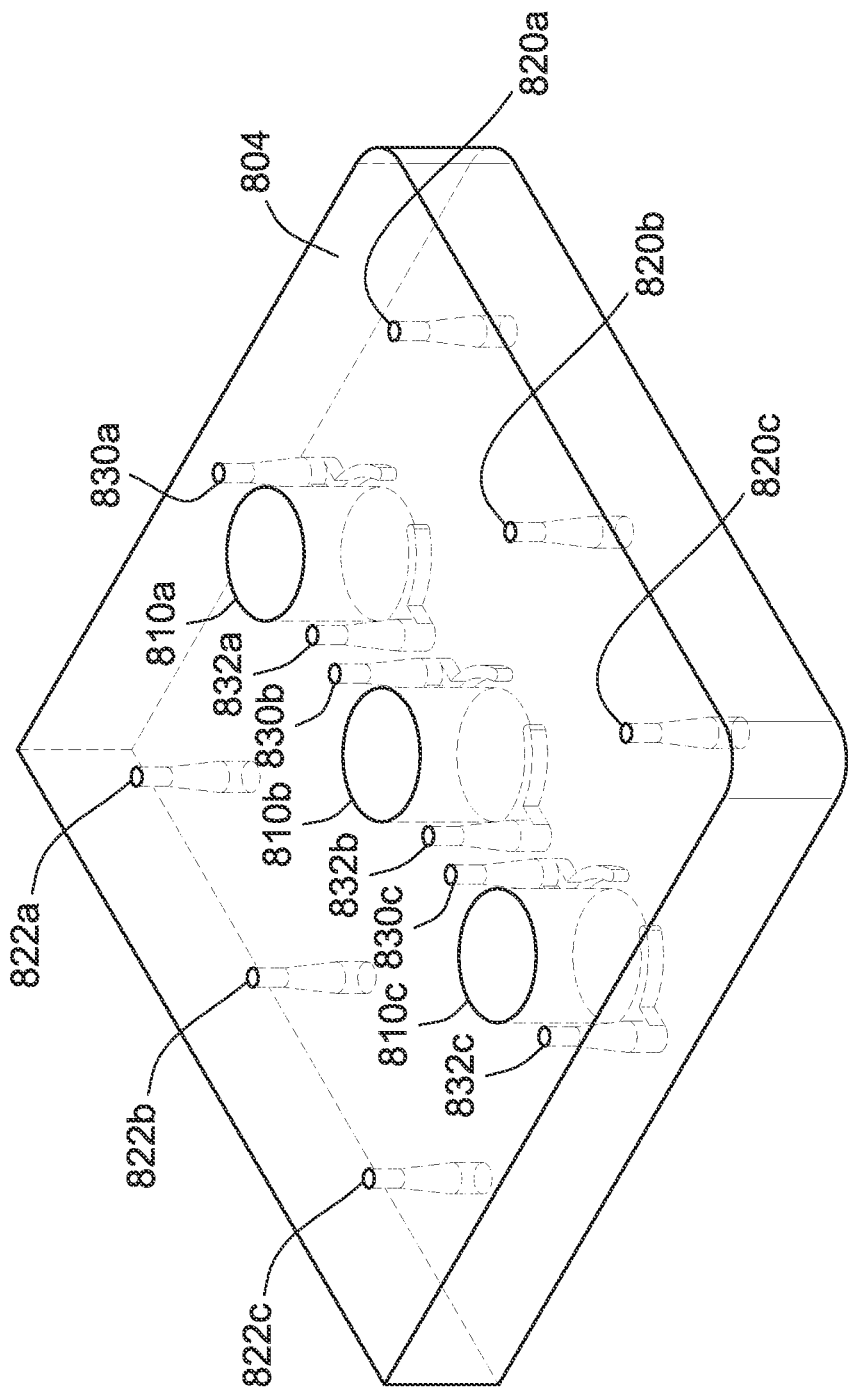
FIG. 8B illustrates a perspective view of the chip top of the exemplary stretchable open-top microfluidic device of FIG. 8A.
Figure 8C:
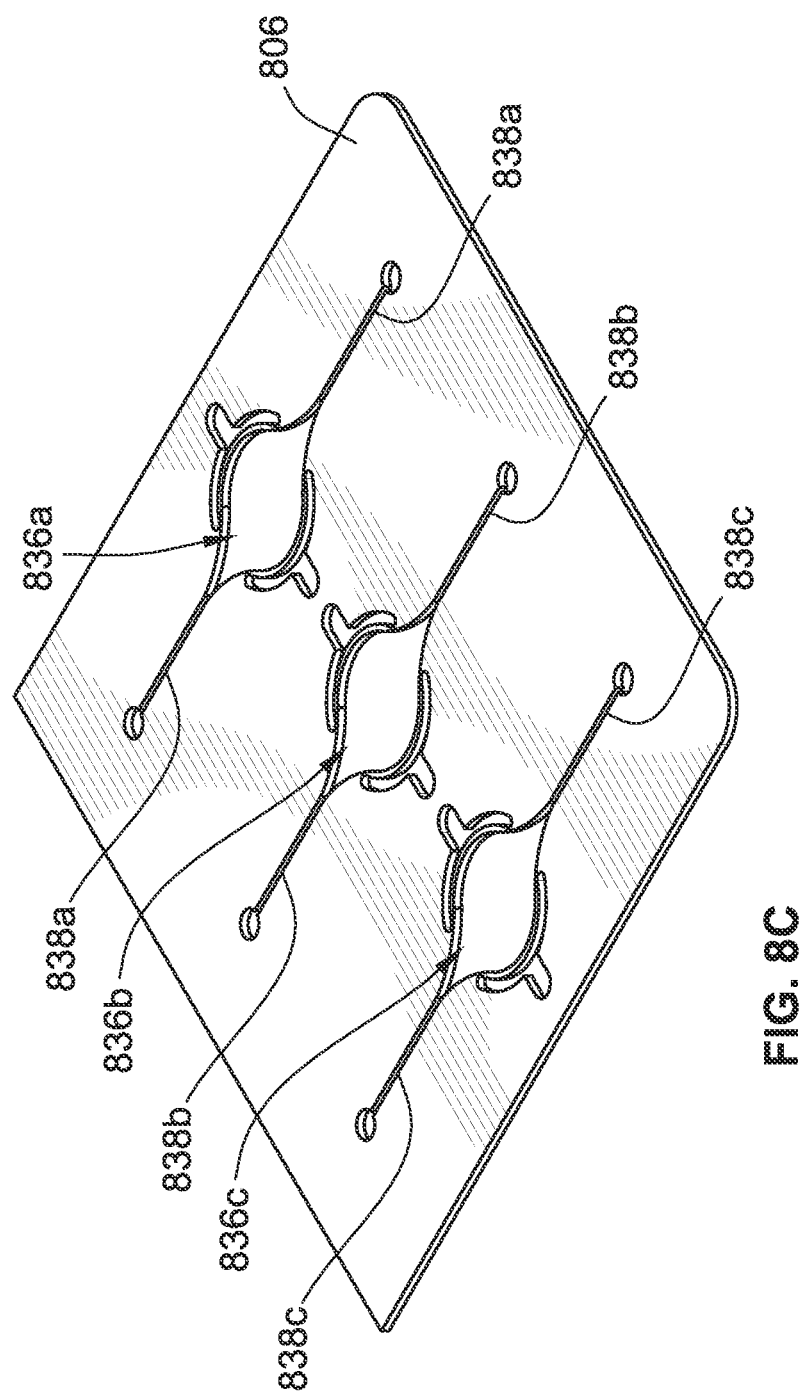
FIG. 8C illustrates a perspective view of the chip bottom of the exemplary stretchable open-top microfluidic device of FIG. 8A.
Figure 9:
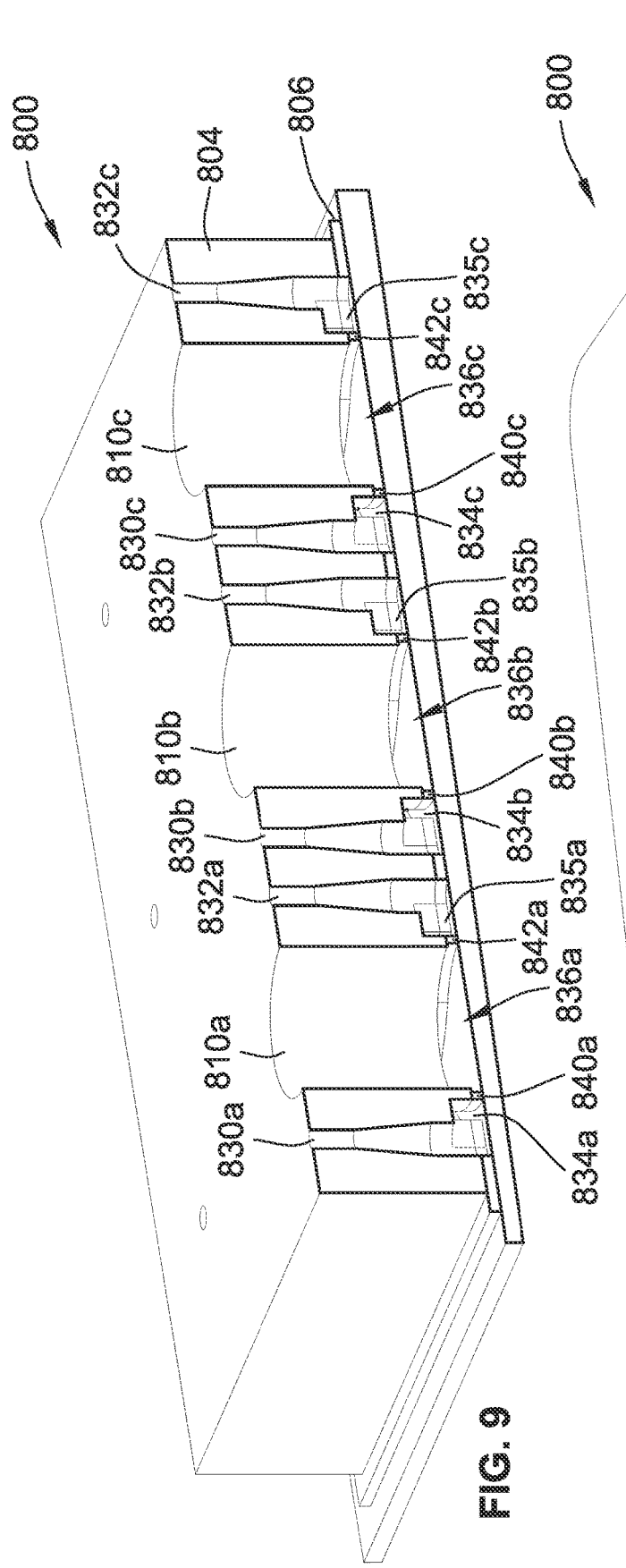
FIGS. 9 and 10 illustrate exemplary perspective views of cross-sections through the stretchable open-top microfluidic device of FIG. 8A.
Figure 10:
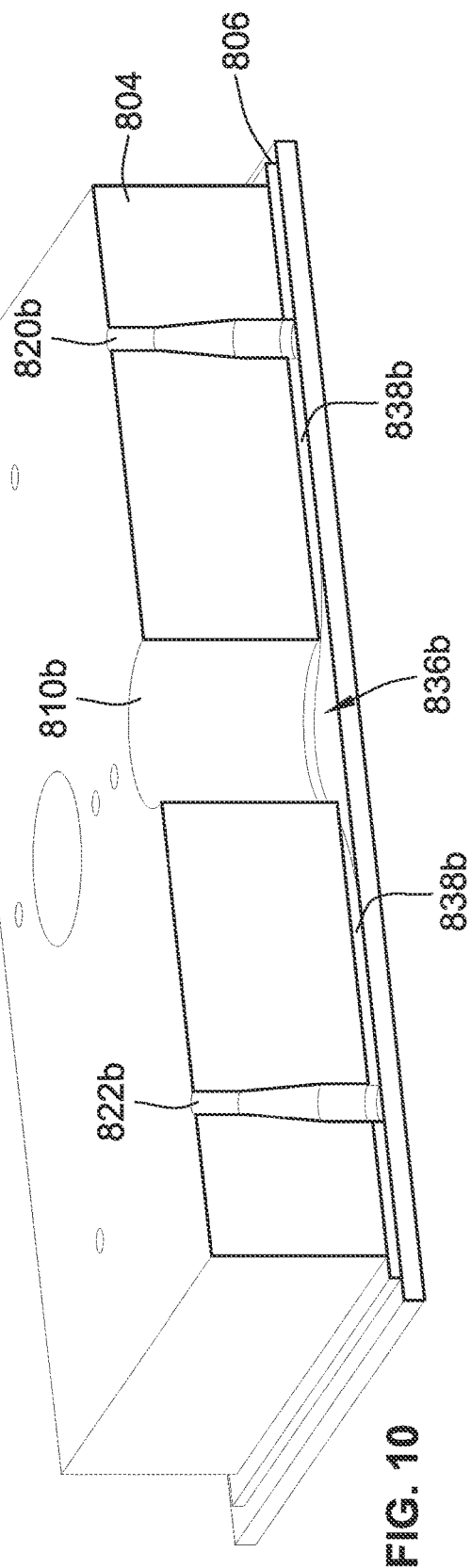

Referring now to FIGS. 8-10, an exemplary aspect of an open-top device 800 including round open regions 810a, 810b, 810c is illustrated. The round open regions 810a, 810b, 810c offer advantages in the use of the device. For example, the device is amenable to biopsy with round biopsy punches typical for in vivo work, there is broad area available for topical treatments or experimental procedures, and they may provide a more isotropic biological environment than, for example, elongated sections. A more isotropic environment can be especially beneficial when present cells affect contractile or expansive forces, as is often the case with fibroblasts such as those present in the dermal-like layer of skin models. Although the depicted aspects in FIG. 8 are round, some of the aforementioned advantages also apply to other shapes, including for example ovals, shapes that inscribe round sections, or other broad shapes.

FIGS. 8-10 specifically illustrates stretchable embodiments of an open-top microfluidic device 800. A stretchable open-top microfluidic device, such as the one illustrated in FIGS. 8-10 can include open regions shaped in various ways including linear sections, although circular, elliptical (e.g., from circular to a 1:2 ratio), or ovoid top region seem to reduce the impact of tissue-induced stress that can lead to delamination of the tissue culture of interest (e.g., skin tissues). A stretchable device may allow for flow in a bottom fluidic layer that is separated from a top fluidic layer by a permeable membrane (not shown), similar to the open-top microfluidic devices described for FIGS. 3-5. While the open-top microfluidic device 800 is described as a stretchable device, it can be used with membranes other than stretchable membranes (e.g., PDMS membranes) for applications where membrane stretch is not desired.

Turning to FIG. 8A, a top view of the exemplary assembled stretchable open-top microfluidic device 800 is illustrated. The device 800 includes a top structure 804 that has three apertures therethrough which define a plurality of open-top openings 810a, 810b, 810c that may include a gel or porous volume. The open-top openings or apertures may extend through the entire thickness of the top structure 804. As mentioned, mechanical actuation can be effected in a variety of ways; in the illustrated example, mechanical stretch is attained using one or more operating channels (e.g., vacuum channels) that are on the perimeter of the open region. The top structure 804 further includes a plurality of vacuum ports 830*a*, 832*a*; 830*b*, 832*b*; 830*c*, 832*c*, that are in communication with the one or more operating channels. The vacuum ports can be connected to a vacuum device that is used to generate pressure differences that cause, for example, a membrane (not shown) to stretch radially. Each open-top opening (e.g., 810*a*) is illustrated as having two opposing vacuum ports (e.g., 830*a*, 832*a*). The illustrated configuration permits the mechanical stretch generated by the operating channels to apply a biaxial force on the device's active regions. Combined with the circular shape of the open regions, the device approximates isotropic stretch, which may be desirable in the recapitulation of the biological mechanical environment of some organs, including the skin. In alternative embodiments, the shape of the open regions and operating channels can be modified to augment the directionality and non-isotropicity of the stretch. Moreover, devices that include a plurality of operating channels corresponding to one or more of the open regions allow the application of different pressures (including vacuum levels) permitting the selection of stretch directionality during use. The top structure 804 further includes a plurality of bottom fluidic layer inlet ports 820*a*, 820*b*, 820*c* and outlet ports 822*a*, 822*b*, 822*c* that allow for the introduction and extraction of fluids (e.g., for perfusion) from the open-top microfluidic device 800. FIG. 8B illustrates a perspective view of the top structure of the exemplary stretchable open-top microfluidic device of FIG. 8A, and in particular shows how the open-top openings, vacuum ports, and bottom fluidic layer extend through the entire top structure 804. More or fewer (e.g., one, two, four, five or more) open-top openings and related support features are contemplated.

Turning now to FIG. 8C, a perspective view of the bottom structure 806 of the exemplary stretchable open-top microfluidic device 800 is illustrated. Similar to the previously described embodiments of an open-top microfluidic device, a permeable membrane (not shown) is disposed along the interface between the top structure 804 and the bottom structure 806. The bottom structure includes a plurality of bottom wells (e.g., 836*a*, 836*b*, 836*c*) that align with open-top openings (e.g., 810*a*, 810*b*, 810*c*), respectively. The membrane separates the open-top openings (e.g., 810*a*) from the bottom wells (e.g., 836*a*). It is contemplated that a gel layer in the device 800 can be formed on top of the membrane in the open-top openings similar to what is described elsewhere herein (see, e.g., FIGS. 5C-5D).

FIGS. 9 and 10 illustrate exemplary perspective views of cross-sections 9-9 and 10-10 through the stretchable open-top microfluidic device of FIG. 8A. With the top and bottom structure assembled, the bottom fluidic layer inlet (e.g., 820*b*) and outlet ports (e.g., 822*b*) each extend through the membrane (not shown) such that the ports are each hydraulically connected to feeding channels 838*a*, 838*b*, 838*c* (e.g., illustrated as long narrow channels) in the bottom structure 806 to allow for the circulation or introduction of fluids into the open-top microfluidic device. Similarly, the vacuum ports (e.g., 830*a*, 832*a*; 830*b*, 832*b*; 830*c*, 832*c*) in the top structure 804 each extend to vacuum chambers 834*a*, 835*a*; 834*b*, 835*b*, 834*c*, 835*c* formed by the interfacing of the top and bottom structures 804, 806. The vacuum chambers are at least partially defined by a stretchable or deformable surfaces 840*a*, 842*a*; 840*b*, 842*b*; 840*c*, 842*c* that introduces pressure changes to actuate the membranes (not shown) at the interface of each of the open-top openings (e.g., 810*a*, 810*b*, 810*c*) with the bottom wells (836*a*, 836*b*, 836*c*).

Figure 11:
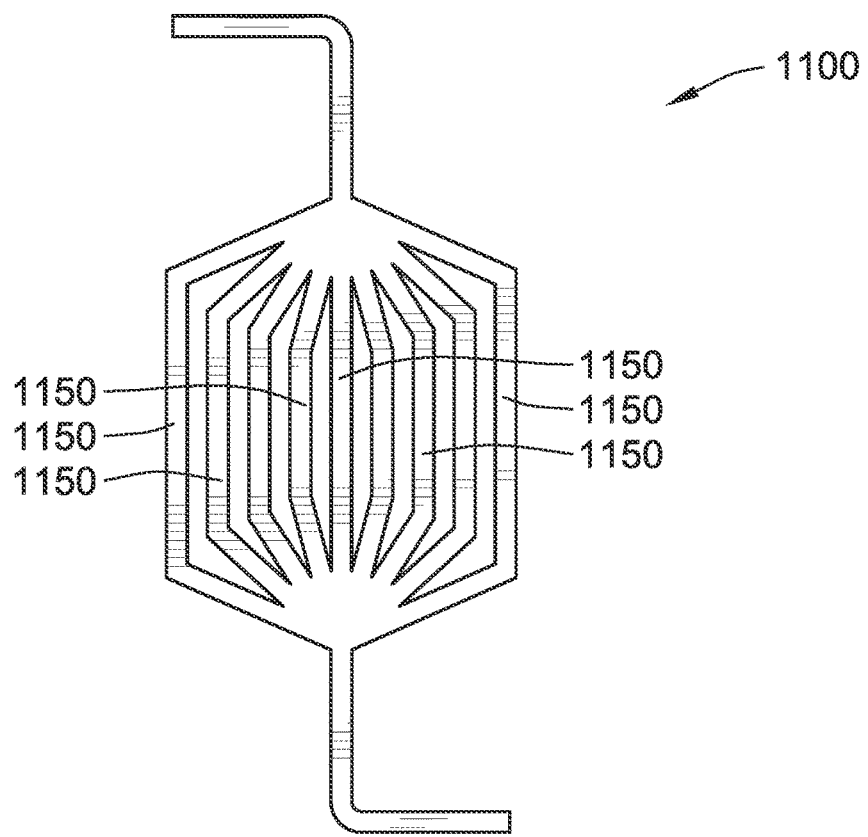
FIG. 11 illustrates a partial top view of an exemplary configuration of multiple parallel channels in a bottom structure for an open-top micro-fluidic device.
Figure 12:
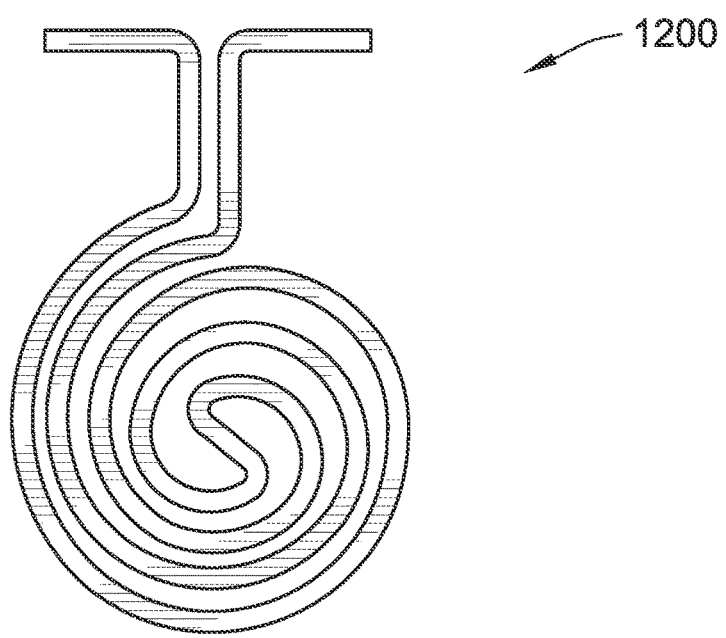
FIG. 12 illustrates a partial top view of an exemplary configuration of spiral channel in a bottom structure for an open-top microfluidic device.
Figure 16:
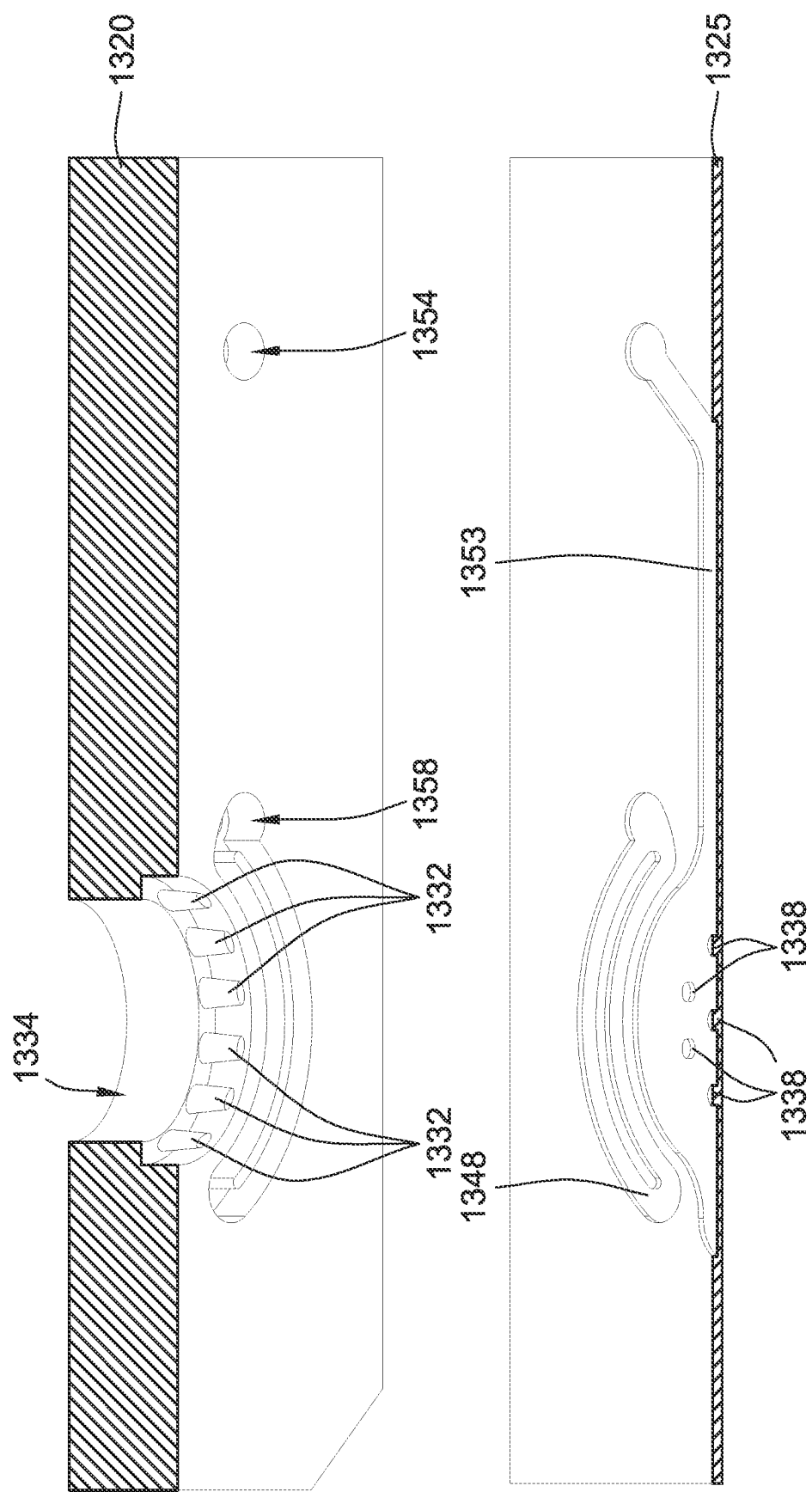
FIGS. 16 and 17 illustrate exploded cross-sectional views of the exemplary open-top microfluidic device of FIG. 13 according to aspects of the present disclosure.
Figure 17:
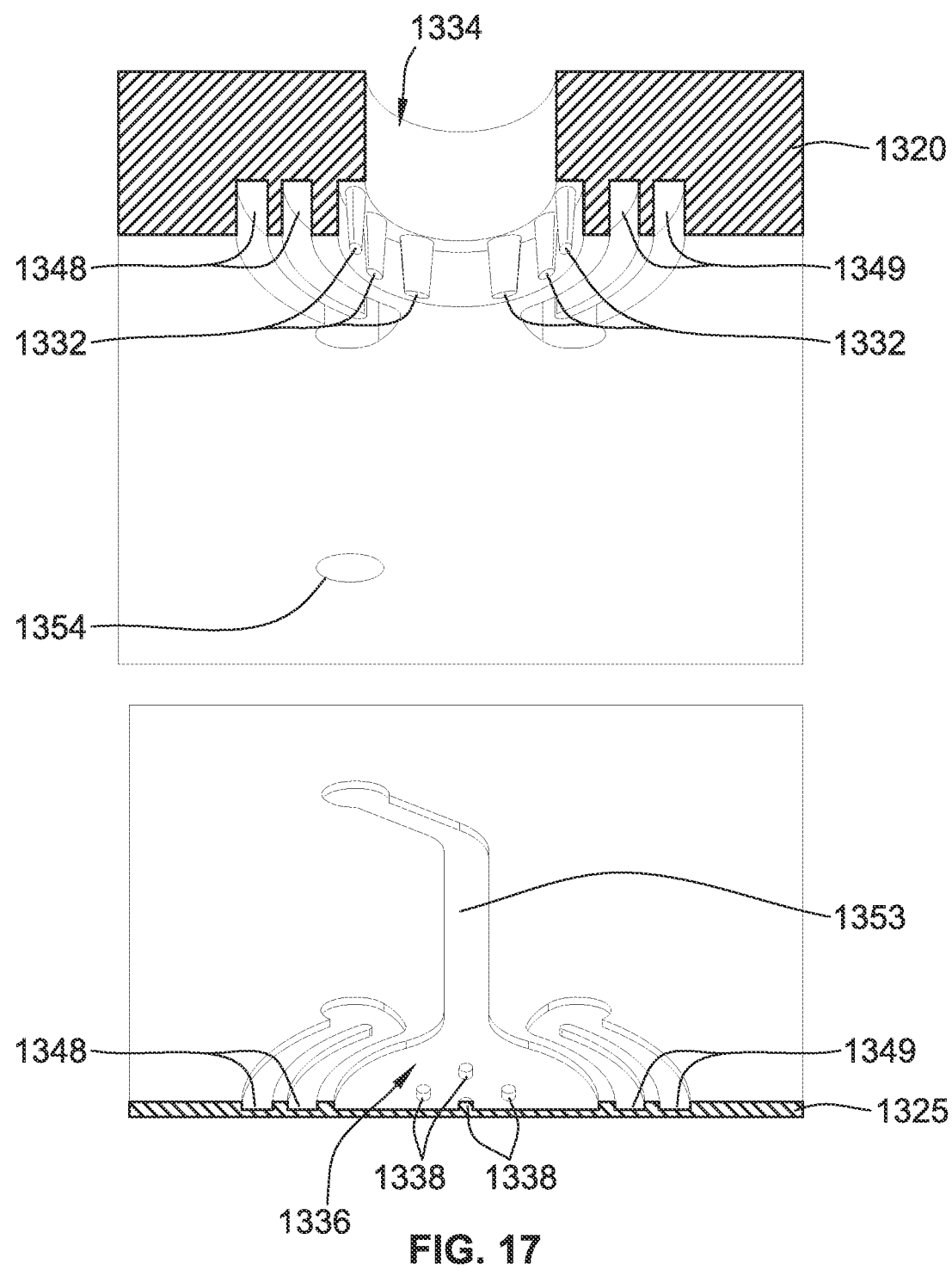

FIGS. 11 and 12 illustrate exemplary views of different bottom channel configurations for a bottom structure (not shown) of a microfluidic device. In some aspects, an open region or open channel is positioned above the bottom channels illustrated in FIGS. 11 and 12 with a semi-permeable membrane separating the bottom channel from the open region. The open region or channel may be circular or oval, as illustrated for example in FIGS. 5F, 8A-8C, 9, 10, and 13-17, or another shape (e.g., rectangular). In the embodiment illustrated in FIG. 11, the bottom channel 1100 is split into a number of constituent channels 1150 within the bottom structure. The smaller constituent channels may offer an advantage in terms of bubble/debris clearance and flow uniformity compared to a single wider channel more typically illustrated in FIG. 2 or 5. Alternatively, as illustrated in FIG. 12, the bottom channel 1200 within the bottom structure can take a spiral, serpentine or meandering form. The configuration of FIG. 12 can provide increased robustness in the face of bubbles and debris that may be present, and can provide a more even flow rate than the bottom channel configuration illustrated in FIG. 11. However, the resulting channel length of the configuration in FIG. 12 is typically longer than in configurations similar to FIG. 11, with the shorter length being advantageous in some applications. The spiral channel configuration illustrated in FIG. 12 first winds inwardly towards the center of the active region and then winds outwardly. An alternative aspect avoids the outward winding by flowing downward, either to a fluidic port or to an additional fluidic channel that may run underneath the spiral channel.

A spiral or a split-channel configuration for the bottom channel, such as the configuration illustrated in FIGS. 11 and 12, provides a more uniform flow for the bottom channel for a microfluidic device where there is an open channel on the other side of the membrane. Other configuration for the bottom channel are contemplated, including more or fewer channel splits, tighter or looser spirals, zigzagging, and/or other patterns.

Turning now to FIGS. 13-17, a top view, cross-sectional views, and exploded cross-sectional views of an exemplary open-top microfluidic device are illustrated where the microfluidic device includes gel-anchoring pillars and membrane support posts. Gel-anchoring mechanisms, such as the exemplary system illustrated in FIGS. 13-17, can be beneficial by reducing delamination or deformation of any gels loaded into or otherwise disposed through the open-top of an open-top microfluidic device. The gel-anchoring mechanism can, for example, add structure for holding the gel in place and providing stretch actuation to a 3D tissue culture, such as skin cultures in collagen gels (e.g., gels ranging from about 0.01 to about 1-3 millimeters thick). In microfluidic systems without a gel anchoring mechanism, stretch of a membrane via a stretch actuation mechanism typically occurs only for the membrane. Such limited stretching can lead to either a rapidly decreasing gradient of stretch in the z axis (i.e., the direction generally perpendicular to the surface of the membrane) of a gel (or tissue) or to delamination of a gel (or tissue) from the membrane. With a gel anchoring system, the stretching of the anchors (e.g., the gel-anchoring pillars illustrated in FIGS. 13-17) of an anchored gel or tissue provides for a more uniform strain to the tissue while minimizing delamination from the membrane.

In some aspects, a gel-anchoring mechanism can include one or more membrane support posts 1338 extending upwardly from the bottom structure 1320 and a plurality of gel-anchoring pillars 1332 extending downwardly from the top structure 1325 of the microfluidic device. The support posts 1338 protrude upwardly from the base of the bottom structure 1325 and are generally disposed toward a central area of a bottom chamber 1336 that is defined by the bottom structure 1325. The support posts 1338 support the center of a membrane (not shown), such as a membrane 40, 540, disposed in between and separating the top and bottom structures 1320, 1325. The use of support posts can be beneficial as the membrane become weighted down after a gel is introduced into the open region 1334 of the top structure 1320. Gel-anchoring pillars 1332 protrude downwardly from a setback 1331 around the perimeter of the open region 1334 of the top structure 1320. The gel-anchoring posts 1332 are disposed along the perimeter walls of the open region that may also define a channel in the top structure 1320. In some aspects, the posts 1338 and pillars 1332 can be molded such that the posts and/or pillars are integral with their respective top and bottom structures from which they protrude. The gel-anchoring pillars extend downwardly in the top structure and provide lateral support for a gel (e.g., a collagen gel) so that lateral displacement of the gel is minimized (e.g., no lift off due to cell-induced contraction). An exemplary elongated elliptical channel that defines the open region 1334, along with deeper vacuum channels 1348, 1349 (e.g., deeper than a microfluidic device without pillars and membrane supports), such as those illustrated in FIGS. 13-17, provide an improved stretch of the gel disposed within the open region 1334.

The gel-anchoring pillars 1332 allow for a collagen gelling agent to flow around in the open region 1334 and around the pillars prior to the gel setting into its final gelled form. The gel-anchoring pillars 1332 can be disposed adjacent to the vacuum channels 1348, 1349 such that the pillars can be actuated similar to what is discussed in FIGS. 8-10 for vacuum-driven stretch systems. It is contemplated that the vacuum channels 1348, 1349 with the configurations illustrated in FIGS. 13-17 maximize their deflection at a position that is at or near the center of the height of the gel within the open region as measured vertically from the top of the membrane to the top of the gel following the gel being disposed in the open region and subsequently gelling. By directing the deflection of the vacuum channels at the vertical mid-point of the gel thickness, increased uniformity and magnitude of strain can be achieved for an experiment. It is contemplated that varying types of gel-anchoring mechanism can be used including the exemplary elliptical configuration with rounded pillars illustrated in FIGS. 13-17.

It is contemplated that in some aspects, the open region can be square, rectangular, circular, oval, or irregularly shaped. The gel-anchoring pillars are desirably disposed along the edges of the open region, or spaced so as to provide a desired strain map within the gel. For example, in some aspects, a strain map can be simulated for a device and based on the outcome of the simulation, the configuration of the gel-anchoring pillars is determined. The membrane support posts can be round, square, rectangular, triangular, other polygonal shapes, or an irregular shape.

In some aspects, actuation of the microfluidic device, including embodiments with gel-anchoring pillars and/or membrane support posts can be performed using external mechanical stretching of the whole device, in which case the pillars would still provide the similar benefits as with the illustrated vacuum actuation system. However, the placement of pillars in the open region would not be limited to being in close proximity to the operating channels (e.g., vacuum channels).

In the exemplary open-top microfluidic device in FIGS. 13-17, an inlet port 1352, an outlet port 1354, and one or more vacuum ports 1358, 1359 are disposed in the top structure 1320. The inlet port 1352 extends into the top structure 1320 and into a channel (not shown) of the bottom structure 1325. The channel then extends into the bottom chamber 1336 of the bottom structure 1325 and to an outlet channel 1353 that is fluidically connected to the outlet port 1354. The one or more vacuum ports 1358, 1359 are fluidically connected to one or more vacuum channels 1348, 1349 that are used to stretch actuate the membrane and/or gel collagen through the periodic generation of a vacuum followed by a pressure release in the vacuum channels. The vacuum channels 1348, 1349 can be defined by the top structure 1320 and bottom structure 1325. In some aspects, the vacuum channel defined by both the top and bottom has a total height ranging from about 1 to about 2 millimeters. The portion of the total height defined by the top structure alone ranges from about 0.5 to about 1.5 millimeters and the portion of the total height defined by the bottom structure is about 0.5 millimeters such that the ratio of the height defined by the top and bottom structures respectively ranges from about a 1:1 ratio to about a 3:1 ratio. Compared to an embodiment without pillars to anchor the gel, an increased total height of a vacuum channel allows the side walls between the vacuum chamber and the open region to deform upon the application of the vacuum which pulls on the anchors and the collagen gel as a unit, rather than creating a pulling only on the membrane. The benefit of pulling the gel-anchoring pillars and collagen gel is increased uniformity of actuation for a 3D culture. In the exemplary aspects of FIGS. 13-17, dual vacuum channels are illustrated that further provide an increased uniformity of stretch along a horizontal plane in the gel (i.e., the plane parallel to the membrane).

The exemplary gel-anchoring pillars 1332 are illustrated along the edge of the open region 1334 of the top channel. The pillars anchor the gel and mechanically stretch the entire thickness of the gel rather than just a shear being provided at the bottom of the gel in a membrane-only stretch actuation mechanism that does not does include pillars. A plurality of support posts 1338 are also disposed in the bottom chamber 1336 that extend up vertically from the base of the chamber to minimize the collapse of the central region of the overlying membrane. In some aspects, it is desirable in a gel-anchoring pillar and support post embodiment of a microfluidic device for the height of the bottom chamber to be increased by approximately 50 percent (e.g., from about 0.2 mm to about 0.3 mm) over an embodiment without the pillars and posts. The increased height of the bottom chamber minimizes the chance of the membrane sticking to the base of the bottom chamber that might occur from sagging of the membrane, particularly after a gel layer is disposed on the membrane.

In some non-limiting exemplary aspects, a microfluidic device incudes an elliptically-shaped open region having a long diameter of about 7.5 mm and a short diameter of about 5 mm. The vacuum channel of the bottom structure is about 0.5 mm high and the corresponding vacuum channel of the top structure is about 1.5 mm high. The bottom chamber of the bottom structure has a height of about 0.3 mm and includes approximately five to eight posts extending upwardly from the base in the central area of the bottom chamber. The posts have a height such that they extend from the base of the bottom chamber to just below the bottom of the membrane. A collagen gel can be disposed in an open region just above a membrane between the top structure and the bottom structure of the microfluidic device. With the collagen gel disposed around the pillars, which extend downwardly into the open region of the top structure, a vacuum-induced stretch actuation within a stretchable transwell is completed for a cell-populated collagen gel that includes dermal fibroblasts. In one aspect, with seven support posts evenly spaced about the middle 2 to 4 millimeters of the membrane exposed to the gel, strains within the stretchable transwell of about 0.8 to 1.2 percent where observed near the anchor pillars and strains of about 0 to 0.2 percent were observed in the central portions of the gel exposed via the open region. In another aspect, with a single membrane support post, strains in the region within the collagen gel were relatively uniform between the bottom of the collagen gel at the interface with the membrane and at the top surface of the collagen gel and ranged from about 5 to 7 percent. Stretch actuation via the vacuum channel was applied at a frequency of one Hertz using a pressure cycling between atmospheric pressure and between approximately 70 kPa and approximately 100 kPa. In some aspects for the systems of FIGS. 13-17, strains ranging from about 3 to 4 percent were obtained at a vacuum actuation pressure of negative 70 kPa.

Other actuation frequencies and vacuum pressures are contemplated that are based on the type of tissue system being replicated in the open-top microfluidic device. The vacuum applied to the vacuum channels is generally expected to be uniform throughout the vacuum channels. However, in the case of rapid actuation, such as actuation cycles greater than about one Hertz, the vacuum pressure may not be uniform due to the resistance of the membrane pores. Pressures applied during vacuum actuation for a microfluidic device are expected to provide linearly proportional displacements or strains that will be dependent on the configuration of the microfluidic device. For example, for two different microfluidic device configurations, one device may produce more strains in a gel layer despite the same pressure being applied to both devices. The amount of strain at a given vacuum pressure will vary based primarily on the vacuum wall configuration, including such parameters as the vacuum wall thickness, height, spacing, and/or material.

External mechanical stretching aspects are also contemplated as discussed, for example, in International Publication No. WO 2015/138032, entitled "Organomimetic Devices and Methods of Use and Manufacturing Thereof", which is hereby incorporated by reference herein in its entirety, or using clamping-based displacement of the microfluidic device. Other possible actuation mechanisms can include electrical, thermal, pH, light, or chemical actuation of a component that swells/shrinks as a result of the actuation mechanism.

Gel-anchoring pillars can be beneficial because during membrane actuation the end(s) of the anchoring pillar(s) will be pulled in and the gel is wrapped around those pillar ends. The pulling in of the end(s) of the anchoring pillar(s) pulls in the lower part of the gel (e.g., the portion of the gel closest to the membrane) in addition to a friction-type pull of the gel on the membrane (e.g., friction or physical or chemical attachment). An increased in the uniformity of the stretch of the gel is preferred. To achieve that uniformity, the top part of the pillar(s) are also deflected as the vacuum chambers or vacuum channels also pull the top(s) of the pillars (e.g., the portion of the pillars farthest from the membrane). The combination of the pillars and vacuum actuation system creates what is essentially a two-point attachment and actuation system that increases the uniformity of the actuation in the system being tested, particularly for arrangements using thicker gels.

It is contemplated that the gel-anchoring pillars are fabricated from elastomers such as PDMS, SEBS, Viton™ (a synthetic rubber and fluoropolymer), rubber, or similar materials. Other elastic materials with minimal creep properties resulting from actuation can also be used to fabricate the gel-anchoring pillars. The spacing of the gel-anchoring pillars can vary. It is contemplated that a denser spacing (e.g., an increased unit width of pillar in relation to a unit width of space as measure along the plane parallel to the membrane) of the gel-anchoring pillars provides for a more uniform stretch of the gel layer. A wider pillar configuration can provide for more efficient fabrication of the microfluidic device. In some aspects, a pillar with a Shore A scale durometer of 40 to 60 is contemplated. Wider durometer ranges are contemplated, as well. For gel layers where a more uniform strain is preferred, materials stiffer than the Shore A scale of 40 to 60 may be more desirable, but actuation using external mechanical forces (e.g., cyclically actuated clamps that latch on to a chip—see International Publication No. WO 2015/138032) may be preferred over vacuum actuation systems. The ratio of the effective modulus of the gel-anchoring pillars to the effective modulus of the gel should be greater than one. In some preferred aspects, the effective modulus of the gel-anchoring pillars is about ten times (or greater) than the effective modulus of the gel. In one exemplary aspect, a bulk modulus of pillars fabricated from PDMS is 1.7 MPa, while that of the collagen is approximately 0.5 to 12 kPa (e.g., the bulk pillar modulus is about 1000 times greater than that of the gel). While the pillars will have an effective modulus lower than the bulk modulus, it is contemplated that an effective modulus of the pillars that is approximately one order or magnitude or more than the gel or collagen is desirable.

Benefits of gel-anchoring mechanisms, such as those illustrated in FIGS. 13-17, have been demonstrated experimentally to minimize gel contraction in both unstrained and strained conditions. For example, gel contraction was minimized in both the unstrained and strained condition for a microfluidic chip having an oval shaped chamber, where by day 11 of culture, no strain was observed. With a cyclic strain application for 7 days at 0.1 Hz and approximately 80 kPa, minimal gel contraction was observed by day 14 of culture.

Gel anchoring mechanisms, such as pillars, also allow for uniform strain distribution throughout the gel thickness. For example, uniform strains on the order of about 6 percent in the z-axis (e.g., in FIGS. 13-17, strains that are perpendicular to a membrane positioned between elements 1320 and 1325 during testing) were observed at the top and bottom of the gel where the bottom of the gel was disposed on a PDMS membrane and the top of the gel was exposed within the open region or chamber.

Microfluidic chips with gel-anchoring mechanisms that allow for cyclic straining are also beneficial, such as for improved skin development and barrier functions for skin-on-chip. For example, skin-on-chip subjected to cyclic straining has been demonstrated to have a thicker epidermis and better developed basal layer. Furthermore, strained skin-on-chip models have also been shown to have approximately an order of magnitude lower apparent permeability in comparison to unstrained chips and static transwell models.

Experimentation on systems without gel-anchoring pillars have shown gel contraction, including for microfluidic chips having round and rectangular chambers. For example, gel contraction on the order of more than 1 mm has been observed after 1 day of culture in a static condition for dermal fibroblasts seeded at 150,000 cells/mL and 300,000 cell, mL in a gel composed of 2.5 mg/mL collagen type 1 from a rat tail. Similarly gel contraction on the order of more than 1 mm has also been observed following cyclic strain in microfluidic chips with round chambers a day 5 in culture at a cyclic strain for 24 hours at 0.1 Hz and approximately 80 kPa.

Additional exemplary aspects of open-top microfluidic devices, such as the devices discussed above in FIGS. 1-17, are now described further. In some aspects, the dimensions of the top area of the open region in a top structure for a chip can range from about 0.1 to about 17 millimeters (or 1 to about 7 millimeters) along in the narrow dimension. In some aspects, the dimensions range from about 0.5 to about 200 or more millimeters (or about 0.5 to about 20 millimeters or more). The lower end of the range of the narrow dimension of the open region is also desirably sized to allow accessibility to the region for pipettes or syringes that are used to place, for example cell cultures or gel materials. The open region can be sized to limit any capillary action, which may be undesirable in some applications (capillary action may nevertheless be desirable in other applications). It is further desirable in some applications for the upper range of the open region dimensions to be sized to maintain accuracy in the flow distribution for the bottom channel across the cell culture area.

In some aspects, the depth of the open region (e.g., measuring vertically upward in the open region from the interface of the top structure with the membrane) can vary from about 0.1 to about 20 millimeters (or about 1 to about 5 millimeters). In some aspects, an additional well or spacer may be added to increase the well volume of the open region, such as where the full depth of the open region is completely filled. It is contemplated that aspect ratios of the dimensions for the top area to the depth of the open region in some applications should range from about 1 to above 100, or in some applications from about less than 0.01 to 2.

In some aspects, it is desirable to have different geometries for the open region based on the type of tissue that is subject to experimentation. For example, certain types of tissue, such as skin, are highly contractile during culturing. When placed into high-aspect ratio (e.g., 16 millimeters by 1 millimeter) channels, delamination of the tissue can occur along the narrow dimension. However, an open region that has a circular (e.g., open region 810*a*) provides radial symmetry that can allow tissue to shrink uniformly and not move out of plane. A wider channel geometry that minimizes edge effects can also be beneficial for other organ systems that may require multiple layers, such as the blood-brain barrier, airways, or digestive tract, because the layers can be more easily formed by the sequential deposition of thin gel or cellular tissue layers, which is difficult to do in closed channels or chambers. In some aspects, the geometry of the open region is something different than the rectangles or circles illustrated in the exemplary aspects of FIGS. 5 and 8. For example, a triangular or star geometry can be used to look at the effects of cell crowding or diffusion of signaling molecules as affected by geometry. In another example, a "figure-8" shape can be beneficial for analyzing the interaction between two three-dimensional cultures.

For fluidic channel(s) disposed in the top structure of an open-top device that might be used for skin, bronchial, or gut tissue simulations, the geometry and dimensions for the open region of a chamber can include a channel-type geometry with a channel height ranging, for example, from about 0.02 millimeters to about 10 millimeters, a channel width of about 0.05 millimeter to 20 millimeter, and a channel length of about 0.5 millimeters to about 300 millimeters. In some aspects, the geometry and dimensions for the open region of a top chamber can include a channel-type shape with a height ranging, for example, from about 0.02 millimeters to about 10 millimeter and a top channel width of about 0.05 millimeter to 20 millimeter. The base or bottom chamber can also have a channel-type shape with a height ranging, for example, from about 0.02 millimeters to about 10 millimeter. For an optional top structure 420 that might be used for brain-barrier and lung tissue simulations, the geometry and dimensions for the top structure, for example, include a height of about 0.05 millimeters to about 5 millimeter. A taller top structure spacer in an open-top microfluidic device is often used for simulations where three-dimensionality is desirable, such as where fibroblast or other cells are embedded in the gel layer for the formation of, for example, a dermal layer. A shorter top structure spacer in an open-top microfluidic device can be used, for example, for simulations where two- or three-dimensionality is desired, such as for small airway simulations where small airway cells feel the paracrine stimulation of neighbor cells, which stimulates their full differentiation.

Various tissue types are contemplated for testing in an open-top microfluidic device (e.g., an open-top OOC device), such as skin, small-airway, and alveolar tissues. However, open-top microfluidic devices can also accommodate other types of tissues, as well, including other epithelial tissues.

The properties of gels or porous volumes that can be used for an open-top microfluidic device can vary and the properties will often depend on the different tissue type that is being tested. For example, different tissue types or specific models may employ different extracellular matrix proteins (ECMs) and ECM mixtures (for example, collagen I, collagen IV, Matrigel® (a solubilized basement membrane matrix), laminin, fibronectin, gelatin, elastin, etc., and combinations thereof). Additionally, some aspects may employ synthetic polymer gels (e.g. polyacrylamide, polyvinyl alcohol, etc.) or various other gels known in the art (e.g. agarose, alginate, etc.) alone, in mixture, or in combinations with ECMs. Similarly, porous volumes used for an open-top microfluidic device may include a variety of open-cell foams, for example, expanded polyurethane, expanded polystyrene, expanded cellulose, expanded polylactic acid, etc. Without being bound by example, for the simulation of a skin or bronchial tissue, the gel can have a higher concentration of collagen, roughly at about 1 to about 11 milligrams per milliliter of gel. For the simulation of gut tissue, one exemplary aspects contemplates a gel with a 1:1 ratio of a high concentration collagen to an ECM such as the Corning® Matrigel® (a solubilized basement membrane matrix) matrix available from Corning Life Sciences, is desirable. For the simulation of alveolar tissue, one exemplary aspect contemplates a gel with a 1:1 ratio of a low concentration of collagen (e.g., about 3 milligrams per milliliter of gel) to ECM, such as the Corning® Matrigel® matrix (a solubilized basement membrane matrix) or fibronectin, is desirable. It is contemplated in one aspect that extracellular matrices or other gel precursors that form gels with concentrations of above 5 milligrams per milliliter of gel, or ranging from about 3 to about 15 milligrams per milliliter of gel, or ranging from about 0.2 to 4 milligrams, can be used in the open-top microfluidic devices described herein. Moreover, cross-linking agents such as transglutaminase, glutaraldehyde, bis(sulfosuccinimidyl)suberate, and many other cross-linkers known in the art, can be used to increase gel stiffness and optionally lower gel concentration. With the use of cross-linkers, it is contemplated that extracellular matrices or other gel precursors that form gels with concentrations ranging from about 0.05 to 5 milligrams per milliliter of gel, or ranging from about 1 to 10 milligrams per milliliter of gel, can be used in the open-top microfluidic devices described herein.

While the described open-top microfluidic devices, including open-top OOC devices, are compatible with standard microfluidic fluids having relatively low viscosities (e.g., about 1 to about 10 centipoise or less), the open-top devices are well-suited for high viscosity solutions and gels having a viscosity equal to or greater than 10 centipoise along with being well-suited for the polymerization of gels in situ for later removal from the microfluidic device and other manipulation of the gel. For example, collagen gels with a high protein content (e.g., 3 milligrams per milliliter) can be directly pipetted into the open tops and gelled in place without shearing cells or requiring high pressure actuation. For drug testing applications, creams and similar high-viscosity materials can be spread directly on the tissue using the open tops to test compounds in the final formulations rather than dissolved drugs alone. Thick gels layers can also be easily generated for three-dimensional culture applications with the potential for providing mechanical stretch. Other desirable aspects of open-top microfluidic devices include the open tops are readily compatible with aerosol and other particulate (e.g., liquid or solid) delivery while minimizing loss, which allows for enabling high dosing accuracy. Because the particles can be delivered directly to the tissue, there is minimal loss due to adsorption to other surfaces, such as tubing and microchannels.

In some aspects, the gel layer described in the above embodiments does not need to be patterned. It is also contemplated that a gel or other material suitable for growing tissues can be patterned externally, shaped to fit the open region of the channel or chamber of the top structure, and subsequently inserted into the open-top microfluidic device for cell culture. The gel or other material could also be a large sheet that is compressed using the spring loaded clamps with the two chambers or channels on either side of the gel or other material, where the gel or other material acts as a membrane in the open-top microfluidic device. The externally-prepared material can include biological tissue such as a biopsy from a patient or small piece of artificial tissue prior to implantation, and thus allow the performance of assays on tissue to determine drug response, tissue quality, and other factors. It is further contemplated that the gel or a similar material from the open-top microfluidic device can be extracted via the open top and used for in vivo applications. For example, the microfluidic device could be used to pattern and mature the tissue prior to implantation.

Numerous skin substitutes are commercially available, such as epidermal substitutes, dermal substitutes, and bilayer substitutes, as detailed in the following Table 1 listing select commercially available skin substitutes:

TABLE 1

Commercially available skin substitutes

| Commercial product | Description |
| --- | --- |
| Epidermal substitutes | |
| BioSeed-S ™ | Subconfluent autologous keratinocytes on a fibrin matrix |
| CellSpray ™ | Noncultured autologous keratinocyte suspension |
| Cryoskin ™ | Cryopreserved monolayer of noncultured allogeneic keratinocytes coating with silicone backing |
| Epibase | Cultured autologous keratinocytes |
| Epicel ® | Cultured autologous keratinocytes from skin on petrolatum gauze backing |
| Epidex ™ | Cultured autologous keratinocytes from the outer root sheath on silicone membrane |
| Episkin ™ | Cultured keratinocytes on a collagen matrix |
| Laserskin ™ Vivoderm ™) | Cultured autologous keratinocytes in a matrix of a hyaluronic acid ester |
| LyphoDerm ™ | Freeze-dried lysate from cultured allogeneic epidermal keratinocytes into a hydrophilic gel |
| Myskin ™ | Cultured autologous keratinocytes seeded on specialty treated silicone sheet |
| ReCell ® | Noncultured autologous keratinocyte suspension |
| Suprathel ® | Absorbable, synthetic wound dressing with properties of natural epithelium |
| Dermal substitutes | |
| AlloDerm ™ | Allogeneic acellular dermal matrix |
| Biobrane ™ | Porcine collagen chemically bound to silicone/nylon membrane |
| Cymetra ™ | Micronized particulate acellular cadaveric dermal matrix |
| Dermagen | Allogeneic fibroblasts cultured in a collagenous sponge |
| Dermagraft ™ | Allogeneic living human-derived fibroblast skin substitute |
| Dermamatrix | Allogeneic acellular human dermis |
| EZ-Derm ™ | Acellular xenogeneic collagen matrix |
| FortaFlex ™ | Acellular collagen matrix material derived from porcine small intestine submucosa |
| Glyaderm ® | Acellular human dermis |
| Graftjacket ® | Allogeneic human acellular pre-meshed dermis |
| Hyalograft 3D ™ | Autologous dermal substitute including a matrix of a hyaluronic acid ester |
| ICX-SKN | Allogeneic dermal substitute with human dermal fibroblasts in human collagen matrix |
| Integra ® | Nonliving extracellular matrix of collagen and chondroitin-6-sulfate with silicone backing |

TABLE 1-continued

Commercially available skin substitutes

| Commercial product | Description |
| --- | --- |
| Karoderm | Allogeneic human acellular dermis |
| Matriderm ™ | Acellular scaffold composed of elastin and collagen types I, III and V |
| Oasis ™ | Acellular collagen matrix material derived porcine small intestinal submucosa |
| Permacol Surgical Implant | Acellular porcine dermis |
| Repliform ™ | Acellular cadaveric human dermal allograft |
| Strattice ™ | Acellular porcine dermis |
| SureDerm | Allogeneic acellular human lyophilized dermis |
| TransCyte ™ | Polymer membrane and allogeneic neonatal human fibroblast cells on a nylon mesh coated with porcine dermal collagen and bonded to a polymer membrane (silicone) |
| Bilayer substitutes | |
| Apligraf ® | Allogeneic cultured human keratinocytes and fibroblasts in a bovine collagen sponge |
| OrCel ® | Similar to Apligraf ® |
| PermaDerm ™ | Autologous keratinocytes seeded onto dermal substitute made with autologous fibroblasts in bovine |
| PolyActive | Autologous cultured keratinocytes and fibroblasts in elastomeric and biodegradable polyethylene oxide terephthalate/polybutylene terephthalate copolymer |
| StrataGraft ® | Allogeneic dermis and epidermis generated from a progenitor cell line: neonatal immortalized keratinocytes (NIKS ®) |
| TissueTech ™ | Autologous dermal substitute Hyalograft 3D combined with an autologous epidermal replacement (Laserskin autograft) |

Evaluating the viability of the growth of physiologically relevant tissues for a microfluidic device, such as the systems for simulating a function of a tissue described in FIGS. 1-12, is desirable. Within the microfluidic device, the tissue is disposed on a membrane. The tissue can include a simulated biological tissue microstructure or a simulated artificial tissue microstructure such as rete pegs in skin or villi in gut. For some aspects, preliminary experimentation included studying the viability of fibroblasts in a microfluidic culture over an extended period of time (e.g., for at least 21 days). In comparison with transwell systems, after about 21 days of being in identical to near identical culture conditions, preliminary indications were that fibroblasts under microfluidic conditions expressed more vimentin and pro-collagen I than fibroblasts in transwells.

In some aspects, preliminary experiments further looked at the viability of fibroblast and keratinocyte co-cultures under microfluidic conditions. On Day 0 of the experimentation, an extracellular matrix coating was prepared using a 30 microgram/milliliter human collagen I followed by fibroblast seeding at two different densities—one at $0.23 \times 10^{\wedge}6$ cells/chip and the other at $0.08 \times 10^{\wedge}6$ cells/chip. Three days after the fibroblast seeding was completed, keratinocyte seeding was implemented at seeding densities of 500 cells/chip and $0.005 \times 10^{\wedge}6$ cells/chip. Then, after six days of fibroblast-keratinocyte co-culture, non-recirculating air-liquid interface ("ALI") was initiated using perfusion parameters of 30 microliters/hour and 60 microliters per hour. The results showed the formation of a functional paracrine loop between the fibroblasts and the keratinocytes with the fibroblast and keratinocyte co-cultures being continued through Day 21. These preliminary experiments showed that fibroblast delamination could be a significant source (e.g., up to 80 percent) of the failure of the microfluidic chip devices (e.g., one or more of the devices described in FIGS. 1-10). It was also identified that keratinocyte quality across the microfluidic chip devices changed across the chip where keratinocytes appeared less healthy further away (e.g., toward the outlet) from the reservoir (e.g., the inlet) of the microfluidic chip devices. It is contemplated that consistencies in tissue quality may have been due to a loss of paracrine signaling, a loss of medium nutrients, or some combination thereof.

Several optimization parameters were identified as part of the preliminary experimentation and additional experimentation was conducted to assess viability of the growth of physiologically relevant tissues for the exemplary microfluidic devices. The optimization parameters include the extracellular matrix coating ("ECM"), the fibroblast seeding density, the keratinocyte seeding density, the recirculation of medium, and the timing of the keratinocyte seeding. The additional experimentation was then conducted based on these identified optimization parameters. At Day 0, an ECM coating was prepared using a 300 microgram/milliliter human collagen I+/−50 micrograms/milliliter of chondroitin. Next, fibroblast seeding was completed at a density of $0.005 \times 10^{\wedge}6$ cells/chip added to the 300 microgram/milliliter collagen I+/−50 micrograms/milliliter of chondroitin. Seven days after the fibroblast seeding was completed, keratinocyte seeding was done at seeding densities of $0.025 \times 10^{\wedge}6$ cells/chip (a 5:1 ratio) and of $0.075 \times 10^{\wedge}6$ cells/chip (a 15:1 ratio). After a period of about 7 days of fibroblast-keratinocyte co-culture (from experiment Days 7 to 14) with a high-calcium ion switch, a recirculating air-liquid interface ("ALI") was initiated at Day 14 using perfusion parameters of 60 microliters/hour. For the 15:1 ratio keratinocyte seeding samples, complete coverage and areas of differentiation were identified such that at Day 21 of the experiment, keratinocytes were in multiple layers with numerous large cells indicating differentiation.

While the experiments were preliminary and representative of some exemplary aspects of tissue growth, the described experimentation demonstrates the viability of the growth of physiologically relevant tissues for the microfluidic devices described herein, including for microfluidic devices for simulating a function of a tissue. In addition, it was further determined that an ECM coating including a collagen I plus a polysaccharide, along with fibroblast seeding in the collagen I, was desirable including for fibroblast seeding densities of approximately $0.005 \times 10^6$ cells/chip. With these optimization parameters, early fibroblast delamination was minimized and there was approximately 10 percent delamination over 14 days of testing, rather than the 80 percent failure rate in earlier experiments. Similarly, keratinocyte health and differentiation along the entire channel of the microfluidic chip device was found to be consistent where keratinocyte densities were increased to about $0.075 \times 10^6$ cells/chip (e.g., at the 15:1 ratio) along with the medium being recirculated and the fibroblasts being cultured for about 7 days before seeding the keratinocytes.

According to certain aspects of the present disclosure, an Alternative Embodiment A is a device for simulating a function of a tissue, comprising a first structure defining a first chamber. The first chamber includes an opened region. A second structure defines a second chamber. A membrane is located at an interface region between the first chamber and the second chamber. The membrane includes a first side facing toward the first chamber and a second side facing toward the second chamber. The membrane separates the first chamber from the second chamber.

An Alternative Embodiment B includes the aspects of Alternative Embodiment A and further comprises a gel disposed in the first chamber. In some aspects, the gel has a patterned surface.

An Alternative Embodiment C includes the aspects of Alternative Embodiment B and includes the gel being cast in the first chamber and/or the second chamber to a thickness ranging from about 100 microns to about 5 millimeters. In some aspects, the gel is cast in the first chamber and/or the second chamber with a thickness generally linearly increasing from about zero millimeter at one end of the chamber to less than about 5 millimeters at another end of the chamber.

An Alternative Embodiment D includes the aspects of any one of Alternative Embodiments A to C and includes the tissue being disposed on the membrane. The tissue can include a simulated biological tissue microstructure or a simulated artificial tissue microstructure. In some aspects, the simulated tissue microstructure includes two-dimensional and/or three-dimensional cultures.

An Alternative Embodiment E includes the aspects of any one of Alternative Embodiments A to D and further comprises a removable cover disposed over the first structure and opened region. The removable cover can optionally define an aperture having one end configured to align with the opened region of the first structure when the removable cover is disposed over the first structure such that a fluid material entering the aperture flows through the removable cover and into the opened region of the first chamber.

An Alternative Embodiment F includes the aspects of any one of Alternative Embodiments A to E and includes the first chamber, the second chamber, and/or the aperture being a channel.

An Alternative Embodiment G includes the aspects of any one of Alternative Embodiments A to F and includes the first chamber and/or the second chamber each being at least partially defined by a stretchable surface configured to be deformable. In some aspects, the stretchable surface is deformed mechanical to actuate the membrane or by a vacuum that causes mechanical actuation of the membrane. The actuation of the membrane can stimulate the simulated tissue microstructure disposed on the membrane.

An Alternative Embodiment H includes the aspects of any one of Alternative Embodiments A to G and further comprises the second chamber including a second opened region. The opened regions are channels with a gel disposed between the channels, and the gel defines the membrane.

According to certain aspects of the present disclosure, an Alternative Embodiment I is a device for simulating a function of a tissue comprising a first structure defining a removable chamber. A second structure defines a fluidic chamber. A third structure defines a gel chamber. A first interface region is formed between the gel chamber and the fluidic chamber. A second interface region is formed between the gel chamber and the removable chamber. A membrane is disposed at the first interface region. The membrane includes a first side facing the gel chamber and a second side facing the fluidic chamber. The membrane separates the gel chamber from the fluidic chamber.

An Alternative Embodiment J includes the aspects of Alternative Embodiment I and that the gel chamber includes a gel having a patterned surface.

An Alternative Embodiment K includes the aspects of any one of Alternative Embodiments I and J and include that at least one of the removable chamber, the gel chamber, and/or the fluidic chamber is a channel.

An Alternative Embodiment L includes the aspects of any one of Alternative Embodiments I to K and further includes a movable cover disposed on the third structure. The movable cover is configured to provide access to the gel chamber such that a gel can be disposed in the gel chamber.

An Alternative Embodiment M includes the aspects of any one of Alternative Embodiments I to L and includes that the tissue is disposed on the membrane. The tissue includes a simulated biological tissue microstructure or a simulated artificial tissue microstructure.

According to certain aspects of the present disclosure, an Alternative Embodiment N is a method for creating a patterned gel in a device for simulating a tissue microstructure. The device includes a first chamber, a second chamber, and a membrane separating the first chamber from the second chamber, where the first chamber includes an opened region. The method comprises placing a plunger stamp into the first chamber through the opened region such that a textured bottom surface of the plunger stamp is in contact with a surface of a gel solution within the first chamber. The textured bottom surface includes a pattern of features to be imprinted into the surface of the gel solution. The gel solution is allowed to solidify in the first chamber. The plunger stamp is removed from the first chamber thereby creating a patterned gel to simulate a tissue microstructure in the device.

According to certain aspects of the present disclosure, an Alternative Embodiment O is a method for creating a patterned gel in a device for simulating a tissue microstructure. The device includes a first chamber, a second chamber, and a membrane separating the first chamber from the second chamber, where the first chamber includes an opened region. The method comprises (i) placing a gel solution in a mold that approximates the shape of the first chamber; (ii) placing a plunger stamp into the gel solution such that a bottom surface of the plunger stamp is in contact with a surface of the gel solution within the mold, wherein the bottom surface comprises a pattern of features to be imprinted into the gel solution; (iii) allowing the gel solution to at least partially solidify in the mold; (iv) removing the plunger stamp from the gel solution, thereby creating a patterned gel to simulate a tissue microstructure; (v) removing the patterned gel from the mold; and (vi) inserting the patterned gel into the first chamber.

An Alternative Embodiment P includes the aspects of Alternative Embodiment O and includes that the patterned gel comprises a biological tissue and/or an artificial tissue.

Some aspects of the technology described herein can be defined according to any of the following numbered paragraphs:
1. A device comprising i) a chamber, said chamber comprising a lumen, said lumen positioned under ii) a removable top and above iii) a porous membrane, said membrane positioned above one or more iv) fluidic channels.
2. The device of paragraph 1, further comprising a gel matrix.
3. The device of paragraph 2, further comprising parenchymal cells on or in the gel matrix, or both.
4. The device of paragraph 3, wherein said parenchymal cells are selected from the group consisting of epithelial cells of the lung and epithelial cells of the skin.
5. The device of paragraph 4, wherein said epithelial cells of the lung are selected from the group consisting of alveolar epithelial cells and airway epithelial cells.
6. The device of paragraph 4, wherein said epithelial cells of the skin comprise keratinocytes.
7. The device of paragraph 1, further comprising positioned on the bottom of the membrane so as to be in contact with the fluidic channels.
8. The device of paragraph 7, wherein the endothelial cells are primary cells.
9. The device of paragraph 8, wherein said primary cells are small vessel human dermal microvascular endothelial cells.
10. The device of paragraph 8, wherein said primary cells are human umbilical vein endothelial cells.
11. The device of paragraph 8, wherein said primary cells are bone marrow-derived endothelial progenitor cells.
12. The device of paragraph 6, wherein said keratinocytes are epidermal keratinocytes.
13. The device of paragraph 6, wherein said keratinocytes are human foreskin keratinocytes.
14. The device of paragraph 1, wherein said device is a microfluidic device and said fluidic channels are microfluidic channels.
15. A device comprising i) a chamber, said chamber comprising a lumen, said lumen comprising ii) a gel matrix, said gel matrix comprising parenchymal cells, said gel matrix positioned above iii) a porous membrane, said membrane comprising endothelial cells in contact with iv) fluidic channels.
16. The device of paragraph 15, wherein said parenchymal cells are selected from the group consisting of epithelial cells of the lung and epithelial cells of the skin.
17. The device of paragraph 16, wherein said epithelial cells of the lung are selected from the group consisting of alveolar epithelial cells and airway epithelial cells.
18. The device of paragraph 16, wherein said epithelial cells of the skin comprise keratinocytes.
19. The device of paragraph 18, further comprising fibroblasts within the gel matrix, wherein the keratinocytes are on top of the gel matrix.
20. The device of paragraph 19, wherein the keratinocytes comprise more than one layer on top of the gel matrix.
21. The device of paragraph 15, wherein the endothelial cells are primary cells.
22. The device of paragraph 21, wherein said primary cells are small vessel human dermal microvascular endothelial cells.
23. The device of paragraph 21, wherein said primary cells are human umbilical vein endothelial cells.
24. The device of paragraph 21, wherein said primary cells are bone marrow-derived endothelial progenitor cells.
25. The device of paragraph 18, wherein said keratinocytes are epidermal keratinocytes.
26. The device of paragraph 18, wherein said keratinocytes are human foreskin keratinocytes.
27. The device of paragraph 15, further comprising an open region in contact with at least one of said gel, said membrane, said parenchymal cells or said endothelial cells.
28. A method of testing a drug, comprising 1) providing a) a candidate drug and b) device comprising i) a chamber, said chamber comprising a lumen, said lumen positioned above ii) a porous membrane, said membrane comprising parenchymal cells and positioned above one or more iii) fluidic channels; and 2) contacting said parenchymal cells with said candidate drug.
29. The method of paragraph 28, wherein said parenchymal cells are selected from the group consisting of epithelial cells of the lung and epithelial cells of the skin.
30. The method of paragraph 29, wherein said epithelial cells of the lung are selected from the group consisting of alveolar epithelial cells and airway epithelial cells.
31. The method of paragraph 29, wherein said epithelial cells of the skin comprise keratinocytes.
32. The method of paragraph 31, further comprising fibroblasts within the gel matrix, wherein the keratinocytes are on top of the gel matrix.
33. The method of paragraph 28, wherein said chamber lacks a covering and said candidate drug is introduced into said lumen under conditions such that said parenchymal cells are contacted.
34. The method of paragraph 28, wherein said candidate drug is in an aerosol.
35. The method of paragraph 28, wherein said candidate drug is in a paste.
36. The method of paragraph 28, wherein said device further comprises a removable top and said method further comprises, prior to step 2), removing said removable top.
37. A method of testing an agent comprising 1) providing a) an agent and b) microfluidic device comprising i) a chamber, said chamber comprising a lumen, said lumen comprising ii) a gel matrix comprising cells in, on or under said gel matrix, said gel matrix positioned above iii) a porous membrane and under iv) a removable cover, said membrane positioned above one or more v) fluidic channels; 2) removing said removable cover; and 3) contacting said cells in, on or under said gel matrix with said agent.
38. The method of paragraph 37, wherein said agent is in an aerosol.
39. The method of paragraph 37, wherein said agent is in a paste.
40. The method of paragraph 37, wherein said agent is in a liquid, gas, gel, semi-solid, solid, or particulate form.
41. A device comprising i) a chamber, said chamber comprising a lumen and projections into the lumen, said lumen comprising ii) a gel matrix anchored by said projections, said gel matrix positioned above iii) a porous membrane, said membrane positioned above one or more iv) fluidic channels.

42. The device of paragraph 41, wherein fibroblasts are within the gel matrix and keratinocytes are on top of the gel matrix.
43. The device of paragraph 42, wherein the keratinocytes comprise more than one layer on top of the gel matrix.
44. The device of paragraph 41, wherein a layer of endothelial cells is positioned on the bottom of the membrane so as to be in contact with the fluidic channels.
45. The device of paragraph 44, wherein the endothelial cells are primary cells.
46. The device of paragraph 45, wherein said primary cells are small vessel human dermal microvascular endothelial cells.
47. The device of paragraph 45, wherein said primary cells are human umbilical vein endothelial cells.
48. The device of paragraph 45, wherein said primary cells are bone marrow-derived endothelial progenitor cells.
49. The device of paragraph 42, wherein said keratinocytes are epidermal keratinocytes.
50. The device of paragraph 42, wherein said keratinocytes are human foreskin keratinocytes.
51. The device of paragraph 41, further comprising a removable cover.
52. The device of paragraph 41, wherein said device is a microfluidic device and said fluidic channels are microfluidic channels.
53. A microfluidic device comprising i) a chamber, said chamber comprising a lumen and projections into the lumen, said lumen comprising ii) a gel matrix anchored by said projections, said gel matrix comprising fibroblasts and keratinocytes, said gel matrix positioned above iii) a porous membrane, said membrane comprising endothelial cells in contact with iv) microfluidic channels.
54. The device of paragraph 53, wherein the membrane is above said fluidic channels and wherein the layer of endothelial cells is positioned on the bottom of the membrane so as to be in contact with the fluidic channels.
55. The device of paragraph 53, wherein the fibroblasts are within the gel matrix and the keratinocytes are on top of the gel matrix.
56. The device of paragraph 55, wherein the keratinocytes comprise more than one layer on top of the gel matrix.
57. The device of paragraph 53, wherein the endothelial cells are primary cells.
58. The device of paragraph 57, wherein said primary cells are small vessel human dermal microvascular endothelial cells.
59. The device of paragraph 57, wherein said primary cells are human umbilical vein endothelial cells.
60. The device of paragraph 57, wherein said primary cells are bone marrow-derived endothelial progenitor cells.
61. The device of paragraph 53, wherein said keratinocytes are epidermal keratinocytes.
62. The device of paragraph 53, wherein said keratinocytes are human foreskin keratinocytes.
63. The device of paragraph 53, wherein said matrix comprises collagen.
64. The device of paragraph 53, wherein said collagen matrix is between 0.2 and 6 mm in thickness.
65. A method of testing a drug on keratinocytes, comprising 1) providing a) a candidate drug and b) microfluidic device comprising i) a chamber, said chamber comprising a lumen and projections into the lumen, said lumen comprising ii) a gel matrix anchored by said projections, said gel matrix comprising fibroblasts and keratinocytes, said gel matrix positioned above iii) a porous membrane, said membrane comprising endothelial cells in contact with iv) fluidic channels; and 2) contacting said keratinocytes with said candidate drug.
66. The method of paragraph 65, wherein the fibroblasts are within the gel matrix and the keratinocytes are on top of the gel matrix.
67. The method of paragraph 65, wherein said chamber lacks a covering and said candidate drug is introduced into said lumen under conditions such that said keratinocytes are contacted.
68. The method of paragraph 65, wherein said candidate drug is in an aerosol.
69. The method of paragraph 65, wherein said candidate drug is in a paste.
70. The method of paragraph 65, wherein said microfluidic device further comprises a removable top and said method further comprises, prior to step 2), removing said removable top.
71. The method of paragraph 65, wherein said microfluidic device further comprises an open region in contact with at least one of said gel matrix, said membrane, said keratinocytes or said endothelial cells.
72. A method of testing an agent comprising 1) providing a) an agent and b) microfluidic device comprising i) a chamber, said chamber comprising a lumen and projections into the lumen, said lumen comprising ii) a gel matrix anchored by said projections and comprising cells in, on or under said gel matrix, said gel matrix positioned above iii) a porous membrane and under iv) a removable cover, said membrane positioned above one or more v) fluidic channels; 2) removing said removable cover; and 3) contacting said cells in, on or under said gel matrix with said agent.
73. The method of paragraph 72, wherein said agent is in an aerosol.
74. The method of paragraph 72, wherein said agent is in a paste.
75. The method of paragraph 72, wherein said agent is in a liquid, gas, gel, semi-solid, solid, or particulate form.
76. A device comprising i) a chamber, said chamber comprising a non-linear lumen, said lumen comprising ii) a gel matrix, said gel matrix positioned above iii) a porous membrane, said membrane positioned above one or more iv) fluidic channels.
77. The device of paragraph 76, wherein fibroblasts are within the gel matrix and keratinocytes are on top of the gel matrix.
78. The device of paragraph 77, wherein the keratinocytes comprise more than one layer on top of the gel matrix.
79. The device of paragraph 76, wherein a layer of endothelial cells is positioned on the bottom of the membrane so as to be in contact with the fluidic channels.
80. The device of paragraph 79, wherein the endothelial cells are primary cells.
81. The device of paragraph 80, wherein said primary cells are small vessel human dermal microvascular endothelial cells.
82. The device of paragraph 80, wherein said primary cells are human umbilical vein endothelial cells.

83. The device of paragraph 80, wherein said primary cells are bone marrow-derived endothelial progenitor cells.
84. The device of paragraph 77, wherein said keratinocytes are epidermal keratinocytes.
85. The device of paragraph 76, wherein said non-linear lumen is circular.
86. The device of paragraph 76, further comprising a removable cover.
87. The device of paragraph 76, wherein said device is a microfluidic device and said fluidic channels are microfluidic channels.
88. A microfluidic device comprising i) a chamber, said chamber comprising a circular lumen, said lumen comprising ii) a gel matrix comprising fibroblasts and keratinocytes, said gel matrix positioned above iii) a porous membrane, said membrane comprising endothelial cells in contact with iv) microfluidic channels.
89. The device of paragraph 88, wherein the membrane is above said fluidic channels and wherein the layer of endothelial cells is positioned on the bottom of the membrane so as to be in contact with the fluidic channels.
90. The device of paragraph 88, wherein the fibroblasts are within the gel matrix and the keratinocytes are on top of the gel matrix.
91. The device of paragraph 90, wherein the keratinocytes comprise more than one layer on top of the gel matrix.
92. The device of paragraph 88, wherein the endothelial cells are primary cells.
93. The device of paragraph 92, wherein said primary cells are small vessel human dermal microvascular endothelial cells.
94. The device of paragraph 92, wherein said primary cells are human umbilical vein endothelial cells.
95. The device of paragraph 92, wherein said primary cells are bone marrow-derived endothelial progenitor cells.
96. The device of paragraph 88, wherein said keratinocytes are epidermal keratinocytes.
97. The device of paragraph 88, wherein said keratinocytes are human foreskin keratinocytes.
98. The device of paragraph 88, wherein said matrix comprises collagen.
99. The device of paragraph 88, wherein said collagen matrix is between 0.2 and 6 mm in thickness.
100. A method of treating endothelial cells, comprising 1) providing a) an angiogenic or arteriogenic growth factor in solution, b) a layered structure comprising i) fluidic channels covered by ii) a porous membrane, said membrane comprising iii) a layer of endothelial cells in contact with said fluidic channels, said membrane position below iv) a gel matrix comprising fibroblasts and keratinocytes; and 2) introducing said solution into said fluidic channels comprising said angiogenic or arteriogenic growth factor so as to treat said endothelial cells.
101. The method of paragraph 100, wherein said gel matrix comprises collagen.
102. The method of paragraph 101, wherein said collagen matrix is between 0.2 and 6 mm in thickness.
103. A fluidic cover comprising a fluidic channel, said fluidic cover configured to engage a microfluidic device.
104. The fluidic cover of paragraph 103, wherein said microfluidic device comprises an open chamber, and wherein said fluidic cover configured to cover and close said open chamber.
105. The fluidic cover of paragraph 103, further comprising one or more electrodes.
106. An assembly comprising a fluidic cover comprising a fluidic channel, said fluidic cover detachably engaged with a microfluidic device.
107. The assembly of paragraph 106, wherein said microfluidic device comprises an open chamber, and wherein said fluidic cover configured to cover and close said open chamber.
108. The assembly of paragraph 107, wherein said open chamber comprises a non-linear lumen.
109. The assembly of paragraph 108, wherein said non-linear lumen is circular.
110. The assembly of paragraph 106, wherein said fluidic cover further comprises one or more electrodes.
111. A method of making an assembly, comprising: a) providing a fluidic cover comprising a fluidic channel, said fluidic cover configured to engage b) a microfluidic device, said microfluidic device comprises an open chamber, and wherein said fluidic cover configured to cover and close said open chamber; and b) detachably engaging said microfluidic device with said fluidic cover so as to make an assembly.
112. The method of making an assembly of paragraph 111, wherein said open chamber comprises a non-linear lumen.
113. The method of making an assembly of paragraph 112, wherein said non-linear lumen is circular.
114. The method of making an assembly of paragraph 111, wherein said fluidic cover further comprises one or more electrodes.
115. A microfluidic device comprising i) a chamber, said chamber comprising a lumen, said lumen comprising ii) a gel matrix comprising at least one of neurons and astrocytes, said gel matrix positioned above iii) a porous membrane, said membrane comprising brain microvascular endothelial cells in contact with iv) microfluidic channels.
116. The microfluidic device of paragraph 115, wherein neurons are on, in or under the gel matrix.
117. The microfluidic device of paragraph 115, wherein astrocytes are on, in or under the gel matrix.

Unless defined otherwise, all technical and scientific terms used herein have the same meaning as commonly understood by one of ordinary skill in the art to which this invention belongs.

It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used to described the present invention, in connection with percentages means±5%.

Each of the above described aspects and obvious variations thereof are contemplated as falling within the spirit and scope of the claimed invention, which is set forth in the following claims. Moreover, the present concepts expressly include any and all combinations and subcombinations of the preceding elements and aspects.

What is claimed is:

1. A microfluidic device comprising:
a gel chamber with a gel matrix disposed therein, the gel chamber including an open top surface region;
a fluidic chamber wherein a first interface region is formed between the gel chamber and the fluidic chamber;
a membrane disposed at the first interface region, the membrane including a first side facing the gel chamber and a second side facing the fluidic chamber; and
a movable cover disposed on the gel chamber above the gel matrix, the movable cover configured to provide access to the gel chamber, wherein the movable cover defines an aperture having one end configured to align with the open top surface region of the gel chamber when the movable cover is disposed on the gel chamber such that a fluid material entering the aperture flows through the movable cover and into the open top surface region of the gel chamber.

2. The microfluidic device of claim 1, wherein the gel matrix includes fibroblasts and keratinocytes in or on the gel matrix.

3. The microfluidic device of claim 2, wherein the aperture is a channel.

4. The microfluidic device of claim 3, wherein the channel is circular, oval, spiral, or irregularly shaped.

5. The microfluidic device of claim 1, wherein the gel matrix disposed in the gel chamber is secured by structural anchors.

6. The microfluidic device of claim 1, wherein the aperture is a channel.

7. The microfluidic device of claim 6, wherein the channel is circular, oval, spiral, or irregularly shaped.

* * * * *